(12) United States Patent
Neumann

(10) Patent No.: US 11,334,352 B1
(45) Date of Patent: May 17, 2022

(54) SYSTEMS AND METHODS FOR GENERATING AN IMMUNE PROTOCOL FOR IDENTIFYING AND REVERSING IMMUNE DISEASE

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,215

(22) Filed: Dec. 29, 2020

(51) Int. Cl.
| | |
|---|---|
| G06F 9/06 | (2006.01) |
| G06N 3/08 | (2006.01) |
| G06N 20/00 | (2019.01) |
| G16B 40/00 | (2019.01) |
| G16H 20/60 | (2018.01) |
| G16H 50/20 | (2018.01) |

(52) U.S. Cl.
CPC ............... *G06F 9/06* (2013.01); *G06N 3/08* (2013.01); *G06N 20/00* (2019.01); *G16B 40/00* (2019.02); *G16H 20/60* (2018.01); *G16H 50/20* (2018.01)

(58) Field of Classification Search
CPC . G06F 9/06; G06N 20/00; G06N 3/08; G16B 40/00; G16H 20/60; G16H 50/20
See application file for complete search history.

(56) References Cited

U.S. PATENT DOCUMENTS

| | | | |
|---|---|---|---|
| 6,103,748 | A | 8/2000 | Bryan |
| 7,252,957 | B2 | 8/2007 | Vojdani |
| 8,367,727 | B2 | 2/2013 | Bassaganya Riera |
| 10,847,261 | B1 * | 11/2020 | Neumann ............. G16H 10/60 |

(Continued)

FOREIGN PATENT DOCUMENTS

| | | |
|---|---|---|
| WO | 9506727 A2 | 3/1995 |
| WO | 2020097077 A1 | 5/2020 |

OTHER PUBLICATIONS

Konijeti et al., Efficacy of the Autoimmune Protocol Diet for Inflammatory Bowel Disease (Year: 2017).*

(Continued)

*Primary Examiner* — Shirley X Zhang
(74) *Attorney, Agent, or Firm* — Caldwell Intellectual Property Law; Katherine Rubino

(57) ABSTRACT

A system for generating an immune protocol including a computing device configured to receive an immune biomarker, retrieve an immune profile, assign the immune profile to an immune category, determine, using the immune category and the immune profile, an elimination plan, including identifying an effect on the immune profile for each nutrition element consumed by the user, determine at least a nutrition element that contributes to the immune category, create, using the elimination plan, a reintroduction phase, including identifying a frequency associated with the nutrition element determined in the elimination plan, and identifying a magnitude associated with the nutrition element determined in the elimination plan, identify a plurality of protocol elements, wherein each contains a nutrient amount intended to prevent autoimmune disease, and generate an immune protocol as a function of the elimination plan, the reintroduction phase, and the plurality of protocol elements.

16 Claims, 8 Drawing Sheets

(56) References Cited

U.S. PATENT DOCUMENTS

| | | | |
|---|---|---|---|
| 2008/0086272 A1* | 4/2008 | Fillet | G16B 20/00 |
| | | | 702/19 |
| 2009/0170777 A1 | 7/2009 | Rozing | |
| 2016/0271257 A1 | 9/2016 | Bredehorst | |
| 2018/0070873 A1* | 3/2018 | Cronin | A61B 5/6802 |
| 2018/0085452 A1 | 3/2018 | Bredehorst | |
| 2018/0292221 A1* | 10/2018 | Bastide | G06N 5/022 |
| 2019/0267140 A1* | 8/2019 | Segal | G06N 20/20 |
| 2020/0321111 A1* | 10/2020 | Neumann | G06N 20/00 |
| 2020/0321114 A1* | 10/2020 | Neumann | G16H 20/30 |
| 2020/0321116 A1* | 10/2020 | Neumann | G16H 20/10 |
| 2020/0321119 A1* | 10/2020 | Neumann | G16B 50/30 |
| 2020/0321121 A1* | 10/2020 | Neumann | G06N 20/20 |
| 2020/0321122 A1* | 10/2020 | Neumann | G06N 20/20 |
| 2020/0323802 A1 | 10/2020 | Gold | |
| 2020/0380015 A1 | 12/2020 | Gray | |
| 2020/0380039 A1* | 12/2020 | Neumann | G06Q 30/0631 |
| 2020/0380421 A1* | 12/2020 | Neumann | G06N 5/04 |
| 2020/0380459 A1* | 12/2020 | Neumann | G06N 20/00 |
| 2020/0380888 A1* | 12/2020 | Neumann | G16H 20/60 |
| 2021/0005317 A1* | 1/2021 | Neumann | G16H 20/60 |
| 2021/0035658 A1* | 2/2021 | Neumann | G16B 40/20 |
| 2021/0035661 A1* | 2/2021 | Neumann | G16H 10/40 |
| 2021/0042637 A1* | 2/2021 | Neumann | G06F 16/24578 |

OTHER PUBLICATIONS

Kagalwalla et al., Identification of Specific Foods Responsible for Inflammation in Children With Eosinophilic Esophagitis Successfully Treated With Empiric Elimination Diet (Year: 2011).*
Reference Notes: Proc Nutr Soc. Nov. 1998;57(4):555-62. doi: 10.1079/pns19980081 Title: Dietary n-6 and n-3 fatty acids in immunity and autoimmune disease Date: By:Laurence S Harbige.
Reference Notes: Immunological Reviews; 260(1): p. 221-34; Jul. 2014 DOI: 10.1111/imr.12191 Title: IL-15: a central regulator of celiac disease immunopathology Date: Jul. 2014 by: Valerie Abadie.
Reference Notes: Arthritis Rheum. Apr. 1983;26(4):462-71. doi: 10.1002/art.1780260403 (https://pubmed.ncbi.nlm.nih.gov/6838671/) Title: Diet Therapy for Rheumatoid Arthritis Date: Apr. 1983 by: R S Panush.

* cited by examiner

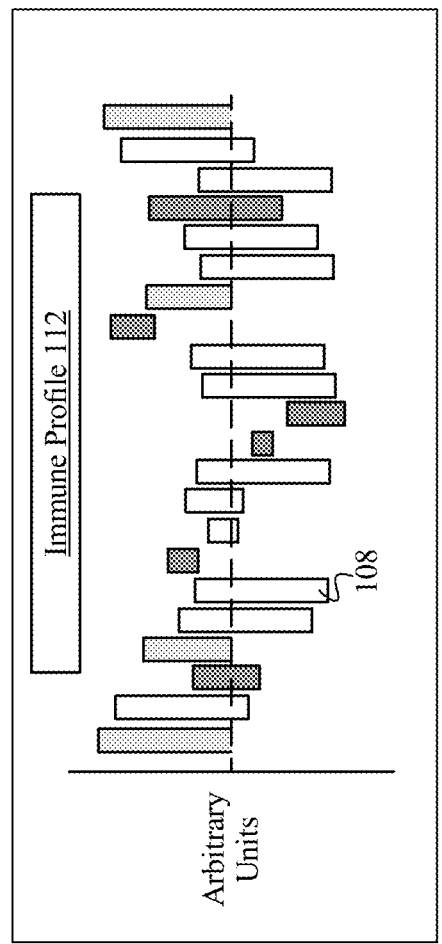 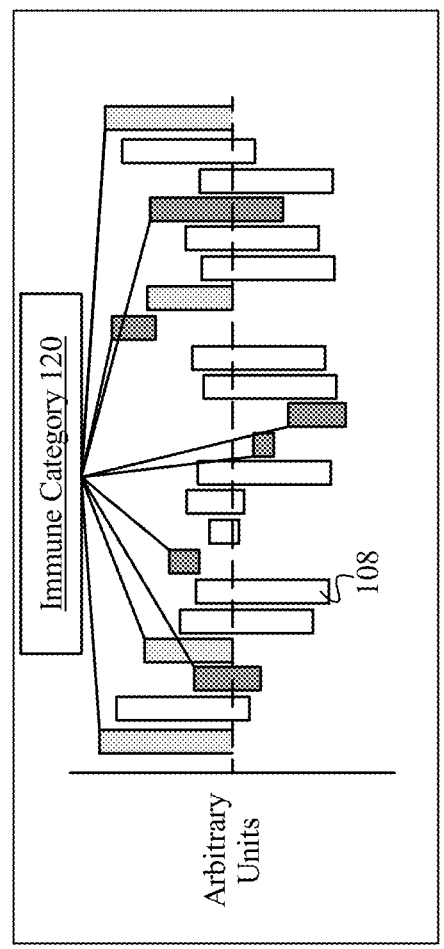

SYSTEMS AND METHODS FOR GENERATING AN IMMUNE PROTOCOL FOR IDENTIFYING AND REVERSING IMMUNE DISEASE

FIELD OF THE INVENTION

The present invention generally relates to the field of nutrition planning for immunological dysfunction. In particular, the present invention is directed to systems and methods for generating an immune protocol for identifying and reversing immune disease.

BACKGROUND

Addressing immunological dysfunction is typically focused on receiving input regarding allergic reactions, altering T cell proliferation, and tracking cellular damage. There exist difficulties in modeling immunological disorders among the human population and generating immunological prophylaxis among the human population.

SUMMARY OF THE DISCLOSURE

In an aspect, a system for generating an immune protocol for identifying and reversing immune disease including a computing device configured to receive at least an immune biomarker, retrieve an immune profile related to the user, assign the immune profile to an immune category, determine, using the immune category and the immune profile, an elimination plan, wherein determining the elimination plan includes identifying an effect on the immune profile for each nutrition element of a plurality of nutrition elements, wherein the plurality of nutrition elements have been consumed by the user, determining, as a function of the identified effect, at least a nutrition element that contributes to the immune category, create, using the elimination plan, a reintroduction phase, wherein creating the reintroduction phase includes identifying a frequency associated with the at least a nutrition element determined in the elimination plan, and identifying a magnitude associated with the at least a nutrition element determined in the elimination plan, output a plurality of protocol elements, wherein each protocol element contains at least a nutrient amount intended to immunological dysfunction, and generate an immune protocol as a function of the elimination plan, the reintroduction phase, and the plurality of protocol elements.

In another aspect, a method for generating an immune protocol for identifying and reversing immune disease including receiving, by a computing device, at least an immune biomarker, retrieving, by the computing device, an immune profile related to the user, assigning, by the computing device, the immune profile to an immune category, determining, by the computing device, using the immune category and the immune profile, an elimination plan, wherein determining the elimination plan includes identifying an effect on the immune profile for each nutrition element of a plurality of nutrition elements, wherein the plurality of nutrition elements have been consumed by the user, determining, as a function of the identified effect, at least a nutrition element that contributes to the immune category, creating, by the computing device, using the elimination plan, a reintroduction phase, wherein creating the reintroduction phase includes identifying a frequency associated with the at least a nutrition element determined in the elimination plan, and identifying a magnitude associated with the at least a nutrition element determined in the elimination plan, outputting, by the computing device, a plurality of protocol elements, wherein each protocol element contains at least a nutrient amount intended to immunological dysfunction, and generating, by the computing device, an immune protocol as a function of the elimination plan, the reintroduction phase, and the plurality of protocol elements.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 4A and 4B are a diagrammatic representation of an immune profile;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating an immune protocol for identifying and reversing autoimmune disease. In an embodiment, computing device is configured to receive an immune biomarker and retrieve an immune profile. Computing device may generate immune profile by training a machine-learning model to derive relationships between immune biomarkers and the current immunological state of the user. Computing device is configured to assign the user to an autoimmunological category as a function of the immune profile. From this autoimmune categorization, computing device may develop an immune protocol, which represents an autoimmune prophylaxis including identifying nutrition elements contributing to the manifestation of autoimmune symptomology. Immune protocol may include determining an elimination plan to remove such elements from the diet, and a reintroduction phase to increase the variety of nutrition elements by identifying which elements may return to the user's diet and the timing and manner with which the reintroduction may occur. Computing device may use machine-learning to derive nutrient amounts according to immunological effects on the user. In an embodiment computing device may generate an objective function to generate combinations of protocol elements (e.g. ingredients, foods, and the like) that achieve nutrient amounts without violating elimination plan and/or reintroduction phase.

Figure 1:
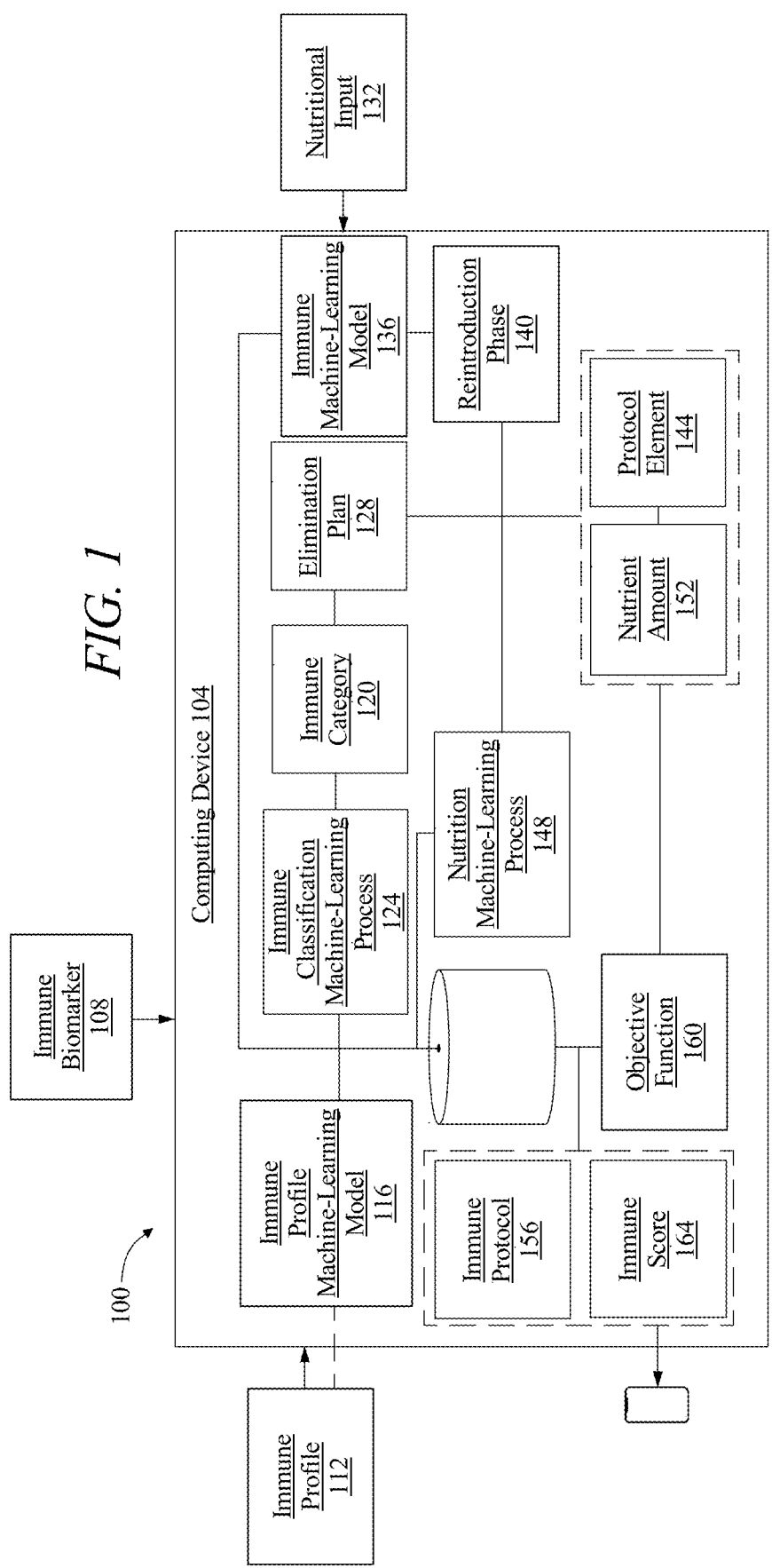
FIG. 1 is a block diagram illustrating a system for generating an immune protocol for identifying and reversing autoimmune disease.

Referring now to FIG. 1, an exemplary embodiment of a system 100 for an immune protocol for identifying and reversing autoimmune disease is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software, and the like) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least an immune biomarker. An "immune biomarker," as used in this disclosure, is a biological and/or chemical substance or process that is indicative of immunological functioning in the body. Immune biomarker 108 may include biological molecules existing within a lymphocyte subset (e.g., CD3+, CD4+, CD8+ T cells, B cells, NK Killer cell,), plasma cell and antibody production, among other myeloid and/or lymphoid lineage cell, and/or a specific response (e.g. antibody response) of the body to innate immunity, adaptive immunity, or autoimmunity. Immune biomarker may include measurements of complement factors (e.g. C3 and C4), and other complement cascade biomolecules. Receiving the at least an immune biomarker 108 may include receiving a result of one or more tests relating the user and/or analysis of one or more tests. For instance and without limitation, an analysis of a biological extraction such as a blood panel test, lipid panel, genomic sequencing, and the like. Such data may be received and/or identified from a biological extraction of a user, which may include analysis of a physical sample of a user such as blood, DNA, saliva, stool, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, immune biomarker 108 may include test results of screening and/or early detection of immunological disorders, diagnostic procedures, prognostic indicators from other diagnoses, from predictors identified in a medical history, and information relating to biomolecules associated with immunological function such as: CD3+, CD8+, CD11c+, CD1a+, IL-2, IL-2RA, JAK3, IL-15, TH1, CXCL10, CXCL9, Th2, IL-13, CCL17, CCL18, IL-12/Il-23p40, IL-32, IL-35, SCUBE-1, sCD40L, aminopeptidase N, vasorin precursor, alpha-1-antitrypsin, ceruloplasmin, and the like, and the like. A person skilled in the art having the benefit of the entirety of this disclosure will be aware of various additional tests and/or immunological biomarkers that may be used by system 100.

Continuing in reference to FIG. 1, immune biomarker 108 may include results enumerating the identification of mutations in nucleic acid sequences. Immune biomarker 108 may include the presents of single nucleotide polymorphisms (SNPs) in genetic sequences. Immune biomarker 108 may include epigenetic factors, such as non-heritable alterations to genetic information. Immune biomarker 108 may include hematological analysis including results from T-cell activation assays, radio immunosorbent test (PRIST), enzyme linked immunosorbent assays (ELISA), radioimmunoassay (RIA), immunoradiometric assays (IRMA), luminescence immunoassays (LIA), and the like. Immune biomarker 108 may include receiving medical history data, past diagnoses, current medications, Type-3 hypersensitivities, allergies, and user input such as a health state questionnaire, symptom complaint, and the like.

Continuing in reference to FIG. 1, computing device 104 may receive immune biomarker 108 as user input. User input may be received via a "graphical user interface," which as used is this disclosure, is a form of a user interface that allows a user to interface with an electronic device through graphical icons, audio indicators, text-based interface, typed command labels, text navigation, and the like, wherein the interface is configured to provide information to the user and accept input from the user. Graphical user interface may accept input, wherein input may include an interaction (e.g. replying to questionnaire, uploading a file, and the like) with a user device.

Continuing in reference to FIG. 1, immune biomarker 108 may be organized into immune training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate a causative and/or predictive links between categories of data elements, which may be modeled as relationships such as mathematical relationships by machine learning processes as described in further detail below.

Continuing in reference to FIG. 1, immune biomarker 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module to produce outputs given data provided as inputs; this is in contrast to a non-machine learning software programing where the commands to be executed are determined in advance by a subject and written in a programming language, as described in further detail below.

Continuing in reference to FIG. 1, immune biomarker 108 may be organized into training data sets and stored and/or retrieved by computing device 104, without limitation, as a relational database, a key-value retrieval database such as a NOSQL database, or any other format or structure for use as a database that a person skilled in the art may recognize as suitable upon review of the entirety of this disclosure. Immune biomarker 108 training data may alternatively or additionally be implemented using a distributed data storage protocol and/or data structure, such as a distributed hash table and the like. Immune biomarker 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of immune biomarkers may be stored, retrieved, organized, and/or reflect data and/or records as used herein, as well as categories and/or populations of data consistent with this disclosure.

Continuing in reference to FIG. 1, "immunological dysfunction," as used in this disclosure, is a disease and/or condition caused by a dysfunction of the immune system. Immunological dysfunction may include allergy, asthma, autoimmune diseases, autoinflammatory syndromes, and immunological deficiency syndrome. Immunological deficiency may be brought on by infection such as by measles, HIV, and the like. Immunological deficiency may be brought on by chronic and sustained exposure to antigens such as by allergy, type-III hypersensitivity, and the like. Immunological deficiency may be brought on by medical and pharmacological intervention and as a result of a secondary effect such as with organ transplants, immunosuppressants, histamine intolerance, among many others. Immunological dysfunction may be brought on by an overactive immunological response such as with eczema, asthma, hay fever, and the like. Immunological dysfunction may be caused by germline and/or somatic genetic mutation such as in congenital disorders (SCID), aberrant gene expression, among many other non-pathogen events.

Continuing in reference to FIG. 1, computing device is configured to retrieve an immune profile related to the user. An "immune profile," as used in this disclosure, is a determination about a current immunological state(s) of the user according to at least an immune biomarker. A "current immunological state," as used in this disclosure, is a metric that encapsulates the current state of autoimmune disorder, immunological priming, immune function, and the like, in the user. A current immunological state may include a current propensity for developing an immunological dysfunction. A current immunological state may include "no dysfunction". In individuals harboring no immunological dysfunction, a current state may include a likelihood of developing in the future, or a percentile of immunological health according to a subset of alike users (e.g. classification). Immune profile 112 may include any number of current immunological state determinations including user's propensity for immunological dysfunction, current level of immunological functioning, and/or their future likelihood for dysfunction. Immune profile 112 may include data represented by numerical values, mathematical expressions, functions, matrices, vectors, and the like.

Continuing in reference to FIG. 1, immune profile 112 may include qualitative and/or quantitative summarization of the presence of immunological function, current and future risks of developing Type-3 hypersensitivity, the level of current immunological function occupied with chronic disease (e.g. viral infections HIV-1, Varicella-zoster, Human Papilloma Virus (HPV), and the like), inflammation (e.g. rheumatoid arthritis), and the like. Immune profile 112 may include qualitative determinations, such as binary "yes"/

"no" determinations for immunological function dysfunction types, "normal"/"abnormal" determinations about the presence of and/or concentration of immune biomarkers 108, for instance as compared to a normalized threshold value of a biomarker among healthy adults. Immune profile 112 may include mathematical representations of the current state of immunological function, such as a function describing, for instance, the risk of immunological dysfunction as a function of time. Such representations of immune profile 112 may allow for determinations such as instantaneous immunological risk, such as daily, weekly, monthly, and the like, risks.

Continuing in reference to FIG. 1, retrieving immune profile 112 may include a process of searching for, locating, and returning immune profile 112 data. For example, immune profile 112 may be retrieved as documentation on a computer to be viewed or modified (e.g. files in a directory, database, and the like). In non-limiting illustrative embodiments, computing device 104 may locate and download immune profile 112 via a web browser and the Internet.

Continuing in reference to FIG. 1, retrieving immune profile 112 may include training an immune profile machine-learning model with training data that includes a plurality of data entries wherein each entry correlates immune biomarkers 108 to a plurality of immune parameters and generating the immune profile 112 as a function of the immune profile machine-learning model and the at least an immune biomarker 108. An "immune parameter," as used in this discourse, is a parameter, metric, numerical value, or the like, that relates to quantifying immune biomarker(s) 108. Immune parameter may include ranges of numerical values which represent ranges of cytokine levels (e.g. IL-2, IL-2RA, JAK3, IL-15, and the like), concentrations of biomarkers, and the like Immune parameter may include threshold values, for instance biomarkers ranges for a healthy adult, for comparing immune biomarker 108.

Continuing in reference to FIG. 1, immune profile machine-learning model 116 may include any machine-learning algorithm (such as K-nearest neighbors algorithm, a lazy naïve Bayes algorithm, and the like), machine-learning process (such as supervised machine-learning, unsupervised machine-learning), or method (such as neural nets, deep learning, and the like), as described in further detail below. Immune profile machine-learning model 116 may be trained to derive an algorithm, function, series of equations, or any mathematical operation, relationship, or heuristic, that can automatedly accept an input (immune biomarker(s) 108) and assign a numerical value to, or otherwise calculate an output (immune parameter(s)). Immune profile machine-learning model 116 may derive individual functions describing unique relationships observed from the training data for each immune biomarker 108, wherein different relationships may emerge between users and user cohorts. Computing device 104 may generate the immune profile 112 as a function of the immune profile machine-learning model 116 and the at least an immune biomarker 108 (input). Immune profile 112 include any number of immune parameters.

Continuing in reference to FIG. 1, training data for generating immune profile 112 may include results from biological extraction samples, health state questionnaires regarding symptomology, medical histories, physician assessments, lab work, and the like. Immune profile training data may originate from the subject, for instance via a questionnaire and a user interface with computing device 104 to provide medical history data. Receiving immune profile training data may include receiving whole genome sequencing, gene expression patterns, and the like, for instance as provided by a genomic sequencing entity, hospital, database, the Internet, and the like Immune profile training data may include raw data values recorded and transmitted to computing device 104 via a wearable device such as a pedometer, gyrometer, accelerometer, motion tracking device, bioimpedance device, ECG/EKG/EEG monitor, physiological sensors, blood pressure monitor, blood sugar and volatile organic compound (VOC) monitor, and the like. Immune profile training data may originate from an individual other than user, including for instance a physician, lab technician, nurse, caretaker, psychologist, therapist, and the like. Immune profile training data may be input into computing device 104 via a graphical user interface for instance for a health state questionnaire for onboarding of user symptomology. It is important to note that training data for machine-learning processes, algorithms, and/or models used herein may originate from any source described for immune profile training data.

Continuing in reference to FIG. 1, in non-limiting illustrative examples, the expression levels of a variety of cytokines as it relates to immunological priming, as identified above, may be retrieved from a database, such as a repository of peer-reviewed research (e.g. National Center for Biotechnology Information is part of the United States National Library of Medicine), and the trained immune profile machine-learning model 116 derived function(s) may calculate an average and statistical evaluation (mean±S.D.) from the data, across which the user's cytokine levels are compared. In such an example, immune profile machine-learning model 116 may derive a scoring function that includes a relationship for how to arrive at an immune parameter numerical value according to the user's level of gene expression (e.g. number of mRNA transcripts per tissue) as it relates to the average and statistical evaluation in normal tissue expression.

Continuing in reference to FIG. 1, immune profile 112 may become increasingly more complete, and more robust, with increasing numbers of immune parameters, describing larger sets of immune biomarkers 108 in the user. Immune parameter may be generated for each biomarker gene (or set of genes) described above; each white blood cell type (or set of white blood cell type); among other factors. Immune profile machine-learning model 116 may derive a unique algorithm for developing individual immune parameters from the plurality of immune biomarkers 108. Immune profile machine-learning model 116 may derive functions, systems of equations, matrices, and the like, that describe and/or incorporate relationships between sets of immune biomarkers 108 (training data), for instance combining the expression level of two or more genes, multiplied by scalar coefficients according to the presence of SNPs (single nucleotide polymorphisms) or mutations present in the genes, dividing by the ratio of phosphorylated-unphosphorylated states, ubiquitinated states, and the like In the full spectrum of cell signaling, maintaining cellular homeostasis, cell division, protein degradation, among other biological phenomenon that may contribute to the development of immunological dysfunction; immune profile machine-learning model 116 may derive increasingly complicated algorithms for combining immune biomarkers 108 into immune parameters summarized in immune profile 112.

Continuing in reference to FIG. 1, computing device 104 is configured to assign the immune profile 112 to an immune category, wherein the immune category is a determination about a current immunological state of the user according to the at least an immune biomarker 108. An "immune category," as used in this disclosure, is a designation of an immunological dysfunction. Immune category 120 may include "no immunological dysfunction". In the instance that a user has no apparent immunological dysfunction, user may be assigned immune category 120 with which the user most closely resembles. Immune category 120 may include tissue or organ type classification, such as "celiac disease", "Graves disease", "Hashimoto thyroiditis", "type I diabetes mellitus", "Addison disease", and the like Immune category 120 may include a designation regarding a type of immunological dysfunction that may not involve a particular tissue such as "type III hypersensitivity", "immune priming issue", "allergic reaction type", "autoimmune disorder", and the like Immune category 120 may include a predictive immunological classification, where a user does not currently have a particular dysfunction but may include data that indicates an immune category 120 with which they may be most closely categorized to in the future. For instance, a family history of arthritis and a combination of epigenetic elements (as summarized in immune profile 112) may classify an individual in "arthritis" immune category 120, despite not currently having arthritis. Immune profile 112 may have associated with it an identifier, such as a label, that corresponds to an immune category 120.

Continuing in reference to FIG. 1, assigning immune profile 112 to immune category 120 may include classifying the immune profile 112 to an immune category 120 using an immune classification machine-learning process. Classification using immune classification machine-learning process 124 may include identifying which set of categories (immune category 120) an observation (immune profile 112) belongs. Classification may include clustering based on pattern recognition, wherein the presence of immune biomarkers 108, such as genetic indicators, symptoms, and the like, identified in immune profile 112 relate to a particular immune category 120. Such classification methods may include binary classification, where the immune profile 112 is simply matched to each existing immune category 120 and sorted into a category based on a "yes"/"no" match. Classification may include weighting, scoring, or otherwise assigning a numerical value to data elements in immune profile 112 as it relates to each immune category 120. Such a score may represent a "likelihood", probability, or other numerical data that relates to the classification into immune category 120, where the highest score is selected depending on the definition of "highest".

Continuing in reference to FIG. 1, immune classification machine-learning process 124 may include any machine-learning process, method, and/or algorithm, as described in further detail below. Immune classification machine-learning process 124 may generate a "classifier" using training data. A classifier may include a machine-learning model, such as a mathematical model, neural net, or program generated by a machine learning algorithm known as a "classification algorithm," as described in further detail below. Such a classifier may sort inputs (such as the data in the immune profile 112) into categories or bins of data (such as classifying the data into an immune category 120), outputting the bins of data and/or labels associated therewith. Training data used for such a classifier may include a set of immune profile 112 training data (as described above) as it relates to classes of immunological dysfunction, organ/tissue, symptoms, severity, and the like for instance, training data may include ranges of biomarker values as they relate to the variety of dysfunctions. Classification machine-learning algorithm may be performed by machine-learning module, as described in further detail below. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, an immune profile 112 training data classifier may classify elements of training data to elements that characterizes a sub-population, such as a subset of immune biomarker 108 (e.g. gene expression patterns as it relates to a variety of immune categories 120) and/or other analyzed items and/or phenomena for which a subset of training data may be selected.

Continuing in reference to FIG. 1, computing device may classify the immune profile 112 to an immune category 120 using an immune classification machine-learning process 124 and assign the immune category 124 as a function of the classification. For instance and without limitation, training data may include sets of immune parameters and/or immune biomarkers 108, as described above. Immune classification machine-learning process 124 may be trained with training data to "learn" how to categorize a user's immune profile 112 to immune categories 120 as a function of trends in mutations, gene expression, SNPs, user symptomology, and the like. Training data may originate from user input, for instance via a health state questionnaire via a graphical user interface, may originate from a biological extraction test result such as genetic sequencing, blood panel, lipid panel. Training data may originate from a user's medical history, a wearable device, a family history of disease. Training data may similarly originate from any source, as described above, for immune biomarker 108 and determining immune profile 112.

Continuing in reference to FIG. 1, computing device 104 is configured to determine, using the immune category 120 and the immune profile 112, an elimination plan. An "elimination plan," as used in this disclosure, is an identity of at least a nutrition element to be removed from a user's current consumption to alleviate a condition associated with immune profile and/or immune category. A "nutrition element," as used in this disclosure, is an item that includes a nutrient intended to be used and/or consumed by user. A "nutrient," as used in this disclosure," is a biologically active compound whose consumption is intended for the treatment of symptoms of immunological dysfunction and/or prevention of immunological dysfunction.

Continuing in reference to FIG. 1, elimination plan 128 may include patterns in currently consumed foods, medications, stimulants, supplements, and the like that may contribute to immunological dysfunction, autoimmunity, and/or symptomology matching immune biomarkers 108. For instance, alcohol, tobacco, oils, gluten, food additives, non-steroidal anti-inflammatory drugs (NSAIDs), and the like, determined to contribute to gut inflammation, Hashimoto's thyroiditis, rheumatoid arthritis, celiac disease, lupus, and the like For example, nutrition elements that may be identified in an elimination plan 128 may include grains, legumes, nuts, seeds, nightshade vegetables (e.g. eggplant, tomato, peppers, and the like), eggs, dairy, and the like Elimination plan 128 may include nutrition elements associated with allergy.

Continuing in reference to FIG. 1, determining elimination plan 128 includes identifying an effect on the immune profile for each nutrition element of a plurality of nutrition elements, wherein the plurality of nutrition elements have been consumed by the user. An "effect on the immune profile," as used in this disclosure, is a change, consequence, and/or result in at least an immune biomarker 108, immune category 120, and/or likelihood of immunological dysfunction in a user due to consumption of an amount of a nutrient. An effect of a nutrient may be "no effect". Calculating an effect of a nutrient may include determining how an immune biomarker 108 may change, such as an increase/decrease according to a particular amount of the nutrient. For instance and without limitation, such a calculation may include determining the effect of chronic, sustained nutrient amounts in a diet for weeks, months, and the like Continuing in reference to FIG. 1, identifying an effect on the immune profile for each nutrition element of a plurality of nutrition elements may include receiving nutritional input from the user. A "nutritional input," as used in this disclosure, is an amount of a nutrient consumed by a user. Computing device 104 may receive nutritional input from user to identify at least more accurately a nutrition element for elimination plan 128. Nutritional input 132, for instance and without limitation, may include food items that have associated nutrition facts, wherein computing device 104 may calculate, weight, or otherwise modify, the nutritional input 132 data (e.g. using a weighting factor). This may result in accurate, per-user nutritional input 132 corrected for metabolic differences, nutrient pharmacokinetics, current immunological states, and the like. Receiving nutritional input, for instance and without limitation, may be performed as described in Ser. No. 16/911,994, filed Jun. 25th, 2020, titled "METHODS AND SYSTEMS FOR ADDITIVE MANUFACTURING OF NUTRITIONAL SUPPLEMENT SERVINGS," the entirety of which is incorporated herein by reference. System 100 may receive nutritional input from a user, retrieve from an application (e.g. calorie tracking application), database, download from the Internet, from physician, and the like Continuing in reference to FIG. 1, determining the effect of the plurality of nutrient amounts on the immune profile 112 may include retrieving a plurality of predicted effects of the plurality of nutrient amounts on the immune profile 112 as a function of the at least an immune biomarker 108. A "predicted effect" of a nutrient or combination of nutrients as used in this disclosure, is a hypothesis about the outcome for a user after consuming a nutrient amount and/or amount of a combination of nutrients. Predicted effect, herein, may refer simply to any effect calculated, determined, and/or output by computing device 104 according to receiving an input associated with the user. Retrieving a plurality of predicted effects may include retrieving from a database, a research repository, or wherever computing device 104 may recognize a relationship between a nutrient amount and immunological dysfunction. Retrieving a plurality of predicted effects may include, for instance, searching using the immune profile 112 (and immune category 120), a web browser and the Internet, for the plurality of predicted effects. In some embodiments, retrieving a plurality of predicted effects may include determining at least a predicted effect, for instance by deriving a function from a machine-learning algorithm. A predicted effect of a plurality of nutrient amounts may include the effect on immune category 120, immune biomarker 108, immune parameter, likelihood of immunological dysfunction, and the like, due to a particular nutrient amount, or combination of nutrient amounts.

Continuing in reference to FIG. 1, identifying an effect on the immune profile 112 may include calculating an effect of nutritional input 132 on immune profile 112. Calculating an effect may include a mathematical operation, such as subtraction, addition, and the like Calculating an effect of a nutrient may include retrieving an empirical formula, equation, and/or function that describes relationships between a nutrient and immune biomarker 108, test result, immune parameter, and the like Calculating an effect of a nutrient may include deriving an algorithm, function, or the like, for instance using a machine-learning process and/or model. Calculating such an effect using machine-learning may include training data that includes a plurality of nutrients as it relates to effects on immune categories 120, immune biomarkers 108, and the like Continuing in reference to FIG. 1, identifying an effect on the immune profile 112 for each nutrition element of a plurality of nutrition elements from nutritional input 132 may include machine-learning. Computing device 104 may train a machine-learning process with training data that includes a plurality of data entries wherein each data entry correlates nutritional input 132 to effects on immunological dysfunction. Training data may include a variety of meals, foods, menu items, medications, and the like, with corresponding labels that may identify the items, for instance from parsing the data in the nutritional input 132 to identify individual nutrition elements. Training data may include nutrient amounts for the constituent nutrition elements in each nutritional input 132. Training data may include pharmacokinetics data relating to how "well" a user absorbs a nutrient amount from nutrition element. Training data may include data sets describing effects of nutrient amounts on immune biomarkers 108. Training data may include immunological dysfunctions according to immune biomarkers 108. Training data may originate from any source as described above, such as from a database, web browser and the Internet, the user, wearable device, a physician, medical history, biological extraction test result, and the like In this way, a machine-learning process (e.g. a neural net) may be trained by computing device 104 to identify all predicted effects (output) from nutritional input 132 (input) according to the relationships derived between each, and the hidden layers (nodes) from nutritional input 132 to constituent ingredients to nutrient amounts to effects on immune biomarkers 108 to immunological dysfunction according to an individualized immune profile 112 and immune category 120. Such a machine-learning process may include any machine-learning algorithm, as performed by a machine-learning module described in further detail below. Computing device 104 using such a trained machine-learning process for determining an effect may accept an input of the immune profile 112 and nutritional input 132 and determine how what a user is consuming is affecting the immune profile 112.

Continuing in reference to FIG. 1, in non-limiting illustrative examples, elimination plan 128 may include determining if a change in immune category 120 may arise from adding and/or removing a nutrient from nutritional input 132, for instance changing an immune category 120 from "high risk type III hypersensitivity" to "moderate risk" and possibly "low risk" with increasing or decreasing dietary short chain fatty acids (C3-C7), medium chain fatty acids (C8-C10), C1-C8 alkyl alcohols, very long-chain fatty alcohols (VLCFA; C24-34), vitamin E, vitamin K, and the like, while eliminating animal milks, peanuts, eggs, soy products, wheat, gluten, shellfish, sesame seed, tree nuts (e.g. pistachio, cashew, walnut, almond, hazelnut, macadamia), among other nutrition elements associated with type III hypersensitivity. Type III hypersensitivity reactions may include an abnormal immune response mediated by the formation of antigen-antibody aggregates called "immune complexes." Immune complexes may precipitate in various tissues such as skin, joints, blood vessels, and/or glomeruli, and trigger the classical complement pathway. Losing control of the formation of immune complexes, or chronically high or inadequately cleared by innate immune cells, the immune complex formation accumulated in the body may lead to serious immunological dysfunction, including symptomatology associated with systemic lupus erythematosus, rheumatoid arthritis, serum sickness, Farmer's lung, and the like. Controlling the timing and manner of eliminating (and potential reintroduction of) nutrient elements identified in nutritional input 132 may help identify which specific nutrient elements are troublesome for a user and be included in elimination plan 128.

Continuing in reference to FIG. 1, identifying an effect of nutrition elements, medications, stimulants, supplements, and the like, for determining elimination plan 128 may include calculating an "immune index" of a nutrition element. An "immune index," as used in this disclosure, is a score that informs the magnitude of effect nutritional input 132 may have on the function of the immune system in the user. Such an immune index may include training a machine-learning model with training data including a plurality of data entries which may correlate nutrition amounts to effects on immune profile 112. Such a trained machine-learning model may derive a scoring function for assigning a score and indexing nutrition elements based on their nutrient content and the score they may be assigned according to their immunological impact. Such an immune index may be used to judge, compare, and/or identify, by placing a logical scoring index on each item to be directly compared. An elimination plan may include an "elimination score", which as used in this disclosure, is a score that may inform which items should be removed from the nutritional input 132. An elimination score may be generated like immune index. An elimination score may include a threshold value (e.g. numerical value), above which nutrition elements may be eliminated from nutritional input 132.

Continuing in reference to FIG. 1, determining elimination plan 128 includes determining, of the identified effect, at least a nutrition element that may contribute to the immune category 120. Elimination plan 128 may be determined based on which nutrition elements may be removed from nutritional input to place user into a different immune category 120. Placing user into a different immune category 120 may include placing the user into a less severe immunological dysfunction, category indicating ameliorating symptomology, and the like Continuing in reference to FIG. 1, determining at least a nutrition element that may contribute to the immune category 120 may include receiving immune training data. "Immune training data," as used in this disclosure, is training data that includes a plurality of data entries wherein each entry correlates a plurality of nutrition amounts to immune biomarkers 108. Immune training data may include any training data set containing data entries, as described above. Immune training data may originate from any source as described above, such as from a database, web browser and the Internet, the user, wearable device, a physician, medical history, biological extraction test result, and the like Immune training data may include data entries such as nutrient amounts, thresholds, values, as described for subsets of users based on age, sex, diagnosis, disease, fitness level, and the like Immune training data may include data entries such as how immune biomarkers 108 (e.g. interleukin cytokines, TNF isoforms, T cell activation, macrophage/granulocyte activity, and the like) are affected by chronic and acute nutrient deficiency, food dyes, commercially-available medications, and the like Continuing in reference to FIG. 1, determining at least a nutrition element that may contribute to the immune category 120 may include training an immune machine-learning model with immune training data. Immune machine-learning model 136 may include any machine-learning process, algorithm, and/or model as performed by machine-learning module described in further detail below.

Continuing in reference to FIG. 1, determining at least a nutrition element that may contribute to the immune category may include determining at least a nutrition element that may contribute to the immune category 120 as a function of the immune machine-learning model 136 and the nutritional input 132 from the user. Immune machine-learning model 136 may be trained with immune training data, as described above, to derive functions, equations, and/or mathematical relationships that may exist between nutrient amounts and immune category 120 based on relationships observed in the training data. Such relationships, for instance, may include how the immune profile 112 (immune parameters and immune biomarkers 108) is affected by carrying amounts of nutrients. Deriving such a function may include calculating a series of numerical values, where for each input (nutrient amount) an output (effect on immune category) may be automatedly determined based on the relationships observed in training data.

Continuing in reference to FIG. 1, in non-limiting illustrative examples, immune machine-learning model 136 may derive a relationship between nutritional input 132 and immune category 120 based effects observed between nutrition elements and biomarkers. For instance, PPAR gamma agonists may inhibit T-cell proliferation by blocking the production of IL-2, potentially alleviating a variety of symptoms associated with immunological dysfunction, such as polycystic ovary syndrome (PCOS). PCOS patients have low expression of PPARγ in skeletal muscle that it was associated with insulin resistance (IR). Treatments with PPAR agonists ameliorated muscle IR and increased the expression of PPARγ with overall increase in mitochondrial biogenesis and function. Moreover, enhancing triglyceride accumulation in adipose tissue, PPARγ agonists are able to diminish lipotoxicity-associated immunological dysfunction. This relationship may be correlated to nutrition elements (e.g. protocol elements, as described in further detail below) and dietary paradigms (immune protocol, as described in further detail below) that may enhance activity and/or concentration of PPARs (immune biomarker 108). For instance, low-calorie diets to achieve weight loss or maintaining a healthy weight, limiting intake of simple sugars, refined carbohydrates, and intake foods with lower glycemic index, reduction of saturated and trans fatty acids and attention to possible deficiencies such as vitamin D, chromium, and omega-3. In such an example, immune machine-learning model 136 may determine the effect of nutritional input 132 on PPAR expression and determine at what threshold level of PPAR the immune category 120 shifts. Achieving a shift may include eliminating some nutritional elements from nutritional input 132. Those nutritional elements may be identified in elimination plan 128.

Continuing in reference to FIG. 1, computing device 104 is configured to create, using the elimination plan 128, a reintroduction phase. A "reintroduction phase," as used in this disclosure, is an identity of a nutrition element whose consumption is to be initially avoided, along with a timeline (frequency) and dosage (serving size) for reintroducing the nutrition element back into the user's diet to allow the widest dietary variety a person can tolerate. Reintroduction phase 140 may include a plurality of identities of nutrition elements and/or nutrient amounts that a user is to be "inoculated" against. Such inoculation may include first removing the nutrition element from the diet and controlling the manner and timing with which to reintroduce the nutrition element to the diet. Such reintroduction phase 140 may represent a method to systematically eliminate extrinsic sources of immunological dysfunction and more accurately identify autoimmunity (immunological dysfunction due to intrinsic factors). Reintroduction phase 140 may assist in identifying food intolerances, allergies, antigens that may contribute to type III hypersensitivities, and the like. Reintroduction phase 140 may assist in identifying immunological dysfunction previously unknown to user.

Continuing in reference to FIG. 1, creating the reintroduction phase 140 includes identifying a frequency associated with the at least a nutrition element determined in the elimination plan 128. A "frequency," as used in this disclosure, is a number of consumption occurrences associated with a time course, such as daily, weekly, monthly, and the like, of which a nutrition element is intended to be consumed. Frequency may be determined as a function of the identified effect in elimination plan 128, wherein the frequency of consumption is tailored to provide a sufficient minimal nutrient level over a time. Identifying the frequency associated with the at least a nutrition element determined in elimination plan 128 may include calculating a consumption time of the at least a nutrition elements as a function of the identified effect in elimination plan 128. A consumption time may include a time of day, which days per week, and the like Frequency may include dosages, for instance and without limitation, a particular number of doses of NSAIDs, chromium, vitamin C, and the like, in a 24 hour period, how many meals per week may be permitted to include an item expected to cause an allergy such as shellfish, dairy, and the like Identifying a frequency may include retrieving data, for instance via a web browser and the Internet, database, and the like, which includes instructions for when to supplement consumption with elimination plan 128 nutrition elements. Identifying a frequency may include retrieving an empirical equation, formula, function, and the like, to calculate the frequency as an output from an input of elimination plan 128. Calculating a frequency may include any mathematical operation (e.g. subtraction, addition, and the like), for instance adding a nutrient amount to nutritional input 132 per frequency to arrive at a calculated total frequency.

Continuing in reference to FIG. 1, identifying a frequency in reintroduction plan 140 may include training a machine-learning model to determine the frequency. Machine-learning model may be with training data including data entries correlating nutrient amounts to effects on immune categories 120, such as immune training data. Training data may include data sets including data entries that correlate microdosing a variety of nutrient amounts to immune biomarkers 108. Training a machine-learning model with such training data may result in deriving a function that may be used to calculate a threshold value of nutrient amounts to reintroduction phase 140 frequencies (e.g. once every 5 meals, twice per week maximum, and the like). Training data may originate from any source as described above, such as from a database, web browser and the Internet, the user, wearable device, a physician, medical history, biological extraction test result, and the like Continuing in reference to FIG. 1, creating the reintroduction phase 140 includes identifying a magnitude associated with the at least a nutrition element determined in elimination plan 128. A "magnitude," as used in this disclosure, is a serving size of at least a nutrition element as a function of the identified effect in the elimination plan 128. Identifying the magnitude associated with the at least a nutrition element may include calculating a serving size of the at least a nutrition element as a function of the identified effect in the elimination plan 128. A nutrition element magnitude may include a calculated nutrient amount. Nutrient amounts may include dosages, for instance and without limitation, a particular dosage of NSAIDs (mg/kg), gluten (g/day), and the like Identifying a magnitude may include retrieving data, for instance via a web browser and the Internet, database, and the like, which includes instructions for how much nutrient amount from the elimination plan 128 to add to user's diet. Identifying a magnitude may include retrieving an empirical equation, formula, function, and the like, to calculate the frequency (output) from elimination plan 128 (input). Calculating a magnitude may include any mathematical operation (e.g. subtraction, addition, and the like), for instance adding a nutrient amount to nutritional input 132 at varying frequencies to arrive at a calculated total magnitude of nutrient amount.

Continuing in reference to FIG. 1, identifying a magnitude may include training a machine-learning model with training data to derive a function describing relationships observed in the training data. Such training data may include effects the nutrient amounts have on immune category, such as immune training data. Training data may include data entries that correlate microdosing a variety of nutrient amounts to immune biomarkers 108. Training a machine-learning model with such training data may result in a function that may derive a threshold value of nutrient amounts to threshold values of immune biomarkers 108 (i.e. maximum value of x mg/kg nutrient amount #1 for staying below maximum value of y mg/L immune biomarker #1). Training data may originate from any source as described above, such as from a database, web browser and the Internet, the user, wearable device, a physician, medical history, biological extraction test result, and the like Training data set and machine-learning model used for deriving frequency may be the same for deriving magnitude; however, the functions, equations, formulas, and the like, derived from the training data may solve for different variables, use different coefficients, and the like, in deterring both frequency and magnitude. For instance a multi-variable equation, wherein as magnitude changes, frequency may change at a different rate.

Continuing in reference to FIG. 1, determining reintroduction phase 140 (or elimination plan 128) may include using a classification machine-learning process. As described above, a classification machine-learning process may use training data to generate a classifier (machine-learning model) which may sort input data into categories and output the bins of data. Such a classification machine-learning process may be trained with training data that relates ingredient serving sizes to effect of autoimmune symptoms, especially in cohorts of alike users. Where cohorts of users that share immune category 120 may be used to derive elimination plan 128. For instance, identifying common nutrition elements between 1,000+ users that share identical immunological dysfunction symptoms. Training data for such a classifier may include nutrition elements identified in elimination plan 128 and/or frequencies and magnitudes identified in reintroduction phase 140 from subsets of alike users. A classifier trained with this training data may "learn" how to sort nutritional input 132 and immune category 120 to elimination plan 128 and reintroduction phase 140. In non-limiting illustration embodiments, such classification may be used as a "starting point", upon which a machine-learning model may derive more accurate elimination plan 128 nutrition elements, and more accurate reintroduction phase 140 frequencies and magnitudes, wherein the reintroduction phase 140 is for restoring the widest variety of diet possible for a user while addressing immunological dysfunction. Training data for such a classifier may originate from any source as described above, such as from a database, web browser and the Internet, the user, wearable device, a physician, medical history, biological extraction test result, and the like Continuing in reference to FIG. 1, reintroduction phase 140 may include calculating a reintroduction score. A "reintroduction score," as used in this disclosure, is a numerical value, score, metric, or the like, that informs if (and when) a user should reintroduce the item(s) to their diet. Such a score may be informed based on user preference, for instance, if the user wants to maintain caffeinated products, reintroduction could start there (e.g. higher score elements). Reintroduction phase 140 may notify user when to begin, and what range of nutrition element should be consumed according to the reintroduction score. Reintroduction score may be generated as a scoring function from a machine-learning process, algorithm, and/or model, as described herein, performed by machine-learning module described in further detail below. Training data may include a plurality of data entries correlating user preference for nutrition element to its elimination score and immune index, as defined above. Training data machine-learning process with such training data may derive a scoring function that penalizes nutrition elements with heavy deleterious immunological effect, while placing scores that prioritize other nutrient elements. Training data for such a machine-learning process may originate from any source as described herein, such as from a database, web browser and the Internet, the user, wearable device, a physician, medical history, biological extraction test result, and the like Continuing in reference to FIG. 1, computing device 104 is configured to identify a plurality of protocol elements, wherein each protocol element contains at least a nutrient amount intended to address immunological dysfunction. A "protocol element," as used in this disclosure, is a nutrient amount specifically curated to address immunological dysfunction, symptomology, and/or prevent immunological dysfunction in the future. "Curating" protocol elements 144, as used in this disclosure, is a process of combining ingredients and/or nutrient amounts according to what is beneficial for each user. Curated protocol elements 144 may include combining ingredients such as spices, plant-based materials, animal products, probiotic cultures, vitamin supplements, trace amounts, and the like, to result in a custom protocol element 144, such as a particular "health shake", unique dish, or the like, which may not be commercially available. Protocol element 144 may include alimentary elements, such as meals (e.g. chicken parmesan with Greek salad and iced tea), food items (e.g. French fries), grocery items (e.g. broccoli), health supplements (e.g. whey protein), beverages (e.g. orange juice), and the like. Protocol element 144 may be "personalized" in that nutrition elements are curated in a guided manner according to immune profile 112, gene expression patterns, immune biomarkers 108, immune category 120, treatment type (T-Car therapy, hormone treatment, surgery, taxanes, cisplatin, and the like), and the like. Protocol element 144 may include supplementary use of oral digestive enzymes and probiotics which may also have merit as immunological modulatory measures.

Continuing in reference to FIG. 1, protocol element 144 may include specific micronutrient, macronutrient, and the like, profile. For instance and without limitation, protocol element 144 may include specific predetermined amounts of propionic acid, chromium, and the like, which may result in a significant decrease in TGFβ1, IL-10, and Foxp3. In some instances, worsening in MS (multiple sclerosis; autoimmune disease) animal models was observed with a diet comprising long-chain fatty acids, whereas mice prophylactically given propionic acid showed significant improvement in the progression of disease; there may be similar results in psoriasis (another autoimmune disease). Protocol elements 144 may include a specific dietary category, such as a "ketogenic diet", "low glycemic index diet", "Paleo diet", and so on.

Continuing in reference in FIG. 1, protocol element 144 may include nutrient amounts intended to address immunological dysfunction according to predicted effects on immune biomarker 108. In non-limiting illustrative examples, experimental autoimmune encephalomyelitis (EAE) induced by sensitization with myelin oligodendrocyte glycoprotein (MOG) is a T cell-dependent autoimmune disease that reproduces the inflammatory demyelinating pathology of multiple sclerosis. The encephalitogenic T cell response to MOG may be either induced or alternatively suppressed as a consequence of immunological cross-reactivity, or "molecular mimicry" with the extracellular IgV-like domain of the milk protein butyrophilin (BTN). In animal models, providing native BTN triggers an inflammatory response in the central nervous system (CNS) characterized by the formation of scattered meningeal and perivascular infiltrates of T cells and macrophages. It may be demonstrated that this pathology is mediated by an MHC class II-restricted T cell response that cross-reacts with the MOG peptide sequence. Conversely, molecular mimicry with BTN may be similarly exploited to suppress immunological dysfunction in MOG-induced users. It may be demonstrated that immunological dysfunction may be ameliorated by treatment with the homologous BTN peptide found in animal milk protocol elements 144, but that the protective effect may also be observed in actively induced disease following transmucosal (intranasal) administration of the peptide. These results identify a mechanism by which the consumption of milk products may modulate the pathogenic autoimmune response to MOG. In such an instance, individuals with immune profile 112 indicated MOG-induced immunological dysfunction may be provided animal milk products as protocol elements 144, regardless of if the element was observed in nutritional input 132.

Continuing in reference to FIG. 1, continuing in further non-limiting illustrative examples, computing device 104 may derive the above relationship between milk proteins and immunological dysfunction to curate protocol element 144. For instance, whey and casein protein supplement products, which include protein profiles derived from animal milk (cow's milk) may lack other antigens such as lactose (lactose intolerance), certain fatty acids, among others. An elimination plan 128 may identify milk products to be eliminated due to their effect on immune biomarkers 108. A reintroduction phase may accommodate the reintroduction of small servings of whey and/or casein, progressing first back to a limited pool of lactose-free animal product, and finally to animal product.

Continuing in reference to FIG. 1, identifying a plurality of protocol elements 144 may include training a nutrition machine-learning process with training data, wherein training data includes a plurality of data entries that correlates a plurality of nutrient effects to a plurality of nutrient amounts for each immune category 120. Nutrition machine-learning process 148 may include any machine-learning process, algorithm, and/or model described herein, as performed by a machine-learning module described in further detail below. Nutrition machine-learning process 148 may train with training data that includes protocol elements 144 identified for each immune category 120. Nutrition machine-learning process 148 may derive relationships in nutrient amounts that relate to particular immune category 120. For instance and without limitation, foods identified to be associated with immunological dysfunction may reveal patterns in nutrients that have yet to be identified by endocrinologists, immunologists, dieticians, and the like. Trained nutrition machine-learning process 148 may generate a function (or series of functions) which describe alterations to nutrition elements (e.g. elimination plan 128 and/or reintroduction phase 140) calculated directly from immune profile 112, prior to classification to immune category 120. Training data for nutrition machine-learning process 148 may include a plurality of data entries that correlates nutrient amounts (and their associated effects, as described herein) to immune category 120. Such training data may include vitamin and mineral amounts to particular immunological dysfunction. A machine-learning model trained with such data may "learn" to output protocol elements 144 as a function of input (immune category 120). Nutrition machine-learning process training data for such a machine-learning process may originate from any source as described herein, such as from a database, web browser and the Internet, the user, wearable device, a physician, medical history, biological extraction test result, and the like Continuing in reference to FIG. 1, identifying a plurality of protocol elements 144 may include calculating the at least a nutrient amount as a function of the immune category 120 of the user. A "nutrient amount," as used in this disclosure, is a numerical value(s) relating to the amount of a nutrient. A "nutrient amount," as used in this disclosure, is a numerical value(s) relating to the amount of a nutrient. Nutrient amount 152 may include mass amounts of a vitamin, mineral, macronutrient (carbohydrate, protein, fat), a numerical value of calories, mass amounts of phytonutrients, antioxidants, bioactive ingredients, nutraceuticals, and the like. Calculating the at least a nutrient amount 152, may include using trained nutrition machine-learning process 148 to automatically calculate nutrient amounts 152 (e.g. mg/kg, mg/cal, mg/g macromolecule, and the like) as a function of the immune category 120 (input). Calculating nutrient amounts 152 in this manner may include deriving functions, equations, and the like, from relationships observed in the training data, as described above.

Continuing in reference to FIG. 1, identifying a plurality of protocol elements 144 may include identifying the plurality of protocol elements 144 according to the nutrition machine-learning process 148 and the at least a nutrient amount 152. Identifying protocol elements 144 may include using the trained nutrition machine-learning process 148 to generate outputs (nutrient amounts 152) and use a mathematical operation (e.g. subtraction) to locate protocol elements 144 (nutrition elements), subtracting the amount of the nutrient from the target nutrient amount 152, to select appropriate protocol elements 144, determine serving sizes, and the like Alternatively or additionally, identifying protocol elements 144 may include training nutrition machine-learning process 148 to generate a classifier, or to additionally add a decision nodes (e.g. neural net layer) to automatedly output protocol elements 144 from the first set of outputs (nutrient amounts 152). For instance, nutrition machine-learning process 148 may be trained with training data that includes a plurality of data entries correlating nutrient amounts 152 to protocol elements 144. In this way, as soon as nutrient amounts 152 are determined, protocol elements 144 that supply the appropriate amounts may be retrieved. "Appropriate" may include using, for instance and without limitation, at threshold value of nutrient amount 152 output by nutrition machine-learning process 144, against which protocol elements 144 may be selected and compared. Such a comparison may yield protocol elements 144 that are selected if they are above or below the threshold value.

Continuing in reference to FIG. 1, computing device 104 may calculate nutrient amounts 152, for instance, by using a default amount, such as from a standard 2,000 calorie diet, and increasing and/or decreasing the amount according to a numerical scale associated with immune parameters in the immune profile 112. Such a calculation may include a mathematical operation such as subtraction, addition, multiplication, and the like; alternatively or additionally, such a calculation may involve deriving a loss function, vector analysis, linear algebra, system of questions, and the like, depending on the granularity of the process. Deriving such a process for the calculating may include nutrition machine-learning process 148. Nutrient amounts 152 may include threshold values, or ranges or values, for instance and without limitation, between 100-500 mcg chromium (+3) per 24 hours, wherein the range changes as a function of immune profile 112. Nutrient amounts 152 may be calculated as heat maps (or similar mathematical arrangements), for instance using banding, where each datum of immune profile 112 elicits a particular range of a particular nutrient amount 152 or set of amounts. In non-limiting illustrative examples, such a calculation may include querying for and retrieving a standard amount of water soluble vitamins for a healthy adult, for instance as described below in Table 1:

TABLE 1

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 µg/day |
| Folic Acid | 400 µg/day |

Continuing in reference to FIG. 1, in reference to Table 1 above, wherein NE is niacin equivalent (1 mg niacin, or 60 mg tryptophan), mg (milligram), kcal (1000 kcal=1 Calorie), and µg (microgram). Computing device 104 may store and/or retrieve the above standard nutrient amounts, for instance in a database. The amounts may be re-calculated and converted according to a user's immune profile 112. For instance, these amounts may relate to an average BMI, older male, classified to rheumatoid arthritis immune category 102, for any range of calories, but may be adjusted according to unique user-specific immune biomarkers 108. For example, an obese woman who has been placed on a strict 1,600 Calorie/day diet, curated according to identified risk factors (immune biomarkers 108) may need the above amounts recalculated according to the calorie constraint (threshold), where some vitamin amounts may increase, some may decrease, and some may remain constant. For instance, if such a person were to suffer from lupus, a particular increase among vitamin C may be calculated according to a weighting factor associated with lupus; with MOG-based and/or PPAR-based immunological dysfunction, vitamin C may increase by a different amount, but vitamin A from retinol sources (animal products) may need to decrease, and so on among many other immunological dysfunction.

Continuing in reference to FIG. 1, computing device 104 may identify the plurality of protocol elements 144 by using nutrient amount 152 as an input and generating combinations, lists, or other aggregates of protocol elements 144 necessary to achieve nutrient amount 152. For instance, computing device 104 may use a template nutrient amount 152 of '200 mg vitamin C' and build a catalogue of protocol elements 144 until the 200 mg vitamin C value is obtained. Computing device 104 may perform this task by querying for food items, for instance from a menu, grocery list, or the like, retrieving the vitamin C content, and subtracting the value from the nutrient amount 152. In non-limiting illustrative examples, computing device 104 may identify orange juice (90 mg vitamin C/serving; 200 mg−90 mg=110 mg) for breakfast, Brussel sprouts (50 mg vitamin C/serving; 110 mg−50 mg=60 mg) for lunch, and baked potato (20 mg vitamin C/serving) and spicy lentil curry (40 mg vitamin C/serving; 60 mg−(20 mg+40 mg)=0 mg) for dinner. In such an example, computing device 104 may search according to a set of instructions (e.g. food preferences, allergies, restrictions, and the like) present in an immune profile 112, provided by a physician, user, or the like, and subtract each identified Protocol element 144 nutrient amount from nutrient amount 152 until a combination of protocol elements 144 that represents a solution is found. Once a solution is found, computing device 104 may generate a file of protocol elements 144 and store in a database, as described in further detail below.

Continuing in reference to FIG. 1, calculating nutrient amounts 152 may include deriving a weighting factor to adjust, or otherwise re-calculate, nutrient amount 152. Weighting factor may be determined by computing device 104, for instance, by querying for vitamin amounts according to data inputs identified in the immune profile 112. For instance in non-limiting illustrative examples, evidence for an inhibitory effect of vitamin D3 on the progression of autoimmune arthritis may come from animal models of arthritis, namely murine Lyme arthritis and collagen-induced arthritis. Development of human Lyme arthritis in mice produced arthritic lesions including footpad and ankle swelling (immune biomarker 108). Supplementation with 1,25-dihydroxycholecalciferol (calcitriol; vitamin D vitamer; naturally occurring form) of an adequate diet fed to mice with arthritis may minimized or prevented these symptoms. Mice immunized with type II collagen also developed arthritis, leading to an autoimmune response to intrinsic type II collagen (immune biomarker 108). The symptoms of this disease may also be prevented by dietary supplementation with 1,25-dihydroxycholecalciferol (1,25-(OH)2D3; vitamin D). 1,25-(OH)2D3 may have an effect on the inhibition of effector T-cell responses by in the induction of Treg populations. For example, in bulk cultures of human CD4+ CD25− T cells and putative naïve T cells, 1,25-(OH)2D3 increased in the presence of IL-2 and the frequency of activation-induced FoxP3+T cells expressing high levels of the inhibitory receptor CTLA-4 (cytotoxic T lymphocyte antigen 4). In such an example, users exhibiting an immune biomarker 108 of these effectors, cytokines, and/or symptomology, may require a particular nutrient amount 152 with regard to vitamin D and the relationship 1,25-(OH)2D3 may have on other vitamins. Specific amounts of vitamin D supplementation may provide a significant reduction in the pro-inflammatory cytokines IFN-7 and IL-17. The capacity of 1,25-(OH)2D3 to promote tolerogenic T cell functions in humans may be further supported by the observation that vitamin D supplementation and pharmacologic treatment with biologically active vitamin D increased the level of serum- or T cell-associated TGF-β and IL-10, representing improvement of current immunological state. Modulation of particular autoimmune symptomology may be done with vitamin D supplementation. But, increasing the amount of vitamin D for all individuals as a blanket suggestion may exacerbate some immune categories. This necessitates careful consideration of immune biomarkers, disease states, and current nutrient levels.

Continuing in reference to FIG. 1, in non-limiting illustrative examples, nutrition machine-learning process 148 may employ a machine-learning algorithm to derive per-user pharmacokinetics of a vitamin, such as vitamin B6. The machine-learning algorithm may accept an input of values including the total amount of protein consumed (in grams) and total amount of vitamin B6 consumed (in mg) per day in a diet, and what the serum levels of the vitamin B6 vitamer, pyridoxal-5-phosphate, over the course of a month, and derive the rates of metabolism, or how 'well' the user is obtaining the vitamin from protocol elements 144 and adsorbing vitamin B6. In other words, the algorithm may derive a function (e.g. using linear regression, vector quantization, least squares, and the like) that describes the pharmacokinetics for that particular user regarding what amount of vitamin B6 consumed, per amount of dietary protein, results in what corresponding amount of bioactive vitamin compound, as measured by the blood vitamer from a biological extraction. Such a function, obtained from machine-learning, may then be used by computing device 104 with an input of the immune profile 112, to calculate an output which is a more accurate, customized, per-user nutrient amount 152 of vitamin B6. Persons skilled in the art, upon the benefit of reviewing this disclosure in its entirety, may appreciate that this process may be repeated and completed for the full spectrum of nutrients, both required as part of a diet and not required as part of a diet, to generate highly accurate and specific protocol elements 144.

Continuing in reference to FIG. 1, additionally, in non-limiting illustrative examples, computing device 104 may relate the concentrations of the metabolic products related to vitamins (e.g. vitamers), minerals, phytonutrients, antioxidative compounds, nutraceuticals, prodrugs, and the like, to their effective concentrations in tissues related to various immune categories 120. For instance, computing device 104 may additionally search and retrieve data that relates the blood levels of the vitamin B6 vitamer, pyridoxal-5-phosphate, to the effective concentrations of vitamin B6 in joints, which is particularly sensitive to vitamin B6-sensitive of markers of inflammation in rheumatoid arthritis. Computing device 104 may store the values in a "look-up table", or graph a relationship as a mathematical function, among other ways of representing a data structure that relates the data identified in the search. Alternatively or additionally, computing device 104 may derive a function, for instance using nutrition machine-learning process, which relates the concentration of the compound in a particular biological extraction, such as blood, to varying amounts in tissues such as joints, pancreas, kidneys, and the like This may prove helpful in calculating nutrient amounts 152 as a function of user consumption to specific target nutrient amount 152 quantities within a particular organ/tissue according to the input data in the immune profile 112. Persons skilled in the art, after review of this disclosure in its entirety, may appreciate that each immune category 120, of 100+ different patterns of immunological dysfunction, may have a unique algorithm for identifying nutrient amounts 152, of the 100's of distinct nutrients identified. For instance and without limitation, each allergy type, tissue/organ affected, stage of immunological dysfunction, type III hypersensitivity, per-user pharmacokinetics, nutrition deficiency, immune biomarker 108, immune profile 112, and the like, may elicit a different mathematical equation for calculating each individual nutrient amount 152.

Continuing in reference to FIG. 1, generate an immune protocol as a function of the elimination plan, the reintroduction phase, and the plurality of protocol elements. An "immune protocol," as used in this disclosure, is a collection of nutrient amounts 152 and protocol elements 144 organized according to constraints in the elimination plan 128 and reintroduction phase 140. Immune protocol 156 may include a frequency (timing) and dosage (serving size) schedule for protocol elements 144. Immune protocol 156 may include gathering, classifying, or otherwise categorizing nutrient amounts 152, protocol elements 144 lists, or the like, which incorporates immunologically-specific dietary recommendations. For instance, protocol elements 144 may be scored with a numerical score scale that associates a meal, snack, beverage, supplement, and the like, with preventing immunological dysfunction, benefit to immunological dysfunction, and the like. Immune protocol 156 may include selecting protocol elements 144 according to a threshold score, where items above are selected and arranged. Threshold score may include a daily threshold, wherein protocol elements 144 are selected each day according to the threshold; and threshold may include a numerical value relating to nutrient amount 152, among other outputs of system 100 described herein. Determining immune protocol 156 may include machine-learning. For instance, training a machine-learning model to identify a scoring rubric for building the immune protocol 156 based on some criteria such as autoimmune prevention, lowering biomarker levels, clearing type III hypersensitivity, among other criteria. Immune protocol 156 may relate specific immune categories 120 to specific nutrients of interest and provide protocol element 144 scheduling times and serving sizes for each meal. Immune protocol 156 may differ from one user to the next according to the magnitude of the disease outline (immune category 120 and immune profile 112).

Continuing in reference to FIG. 1, immune protocol 156 may include a recommended nutrition plan and a recommended supplement plan that at least addresses immune biomarker 108, mitigate symptoms, side-effects, and the like Immune protocol 156 may contain a plan with timing of meals, calorie amounts, vitamin amounts, mineral amounts, and the like Immune protocol 156 may include food items combined with a supplement of non-food items. Immune protocol 156 may be presented as a function of preventing immunological dysfunction for non-dysfunction users, for instance an otherwise healthy person to reduce their lifelong risk of developing allergies, intolerances, and the like Continuing in reference to FIG. 1, generating the immune protocol may include generating an objective function with the plurality of protocol elements 144, wherein the objection function outputs at least an ordering of the plurality of protocol elements 144 according to constraints in the reintroduction phase 140. An "objective function," as used in this disclosure, is a mathematical function that may be used by computing device 104 to score each possible combination of protocol elements 144, wherein the objective function may refer to any mathematical optimization (mathematical programming) to select the 'best' element from a set of available alternatives. Selecting the 'best' element from a set of available alternatives may include a combination of protocol elements 144 which achieves the nutrient amounts 152 in addressing immune profile 112 in a user.

Continuing in reference to FIG. 1, an objective function 160 may include performing a greedy algorithm process. A "greedy algorithm" is defined as an algorithm that selects locally optimal choices, which may or may not generate a globally optimal solution. For instance, computing device 104 may select combinations of protocol elements 144 so that values associated therewith are the best value for each category. For instance, in non-limiting illustrative example, optimization may determine the combination of the most efficacious 'serving size', 'timing of consumption', 'probiotic product', 'vegetable', and the like, categories to provide a combination that may include several locally optimal solutions but may or may not be globally optimal in combination.

Still referring to FIG. 1, objective function 160 may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a user (e.g. lactose intolerance, poor absorption, food allergy, user preference, and the like), and a linear program may use a linear objective function to calculate combinations, considering how these limitations effect combinations. In various embodiments, system 100 may determine a set of instructions towards addressing a subject's immune profile 112 that maximizes a total prevention score subject to a constraint that there are other competing objectives. For instance, if achieving one nutrient amount 152 by selecting from each protocol element 144 may result in needing to select a second protocol element 144, wherein each may compete in prevention (e.g. adopting two or more diet types simultaneously may not be feasible, and the like). A mathematical solver may be implemented to solve for the set of instructions that maximizes scores; mathematical solver may be implemented on computing device 104 and/or another device in system 100, and/or may be implemented on third-party solver.

With continued reference to FIG. 1, objective function may include minimizing a loss function, where a "loss function" is an expression an output of which a process minimizes to generate an optimal result. For instance, achieving nutrient amounts 152 may be set to a nominal value, such as '100', wherein the objective function selects elements in combination that reduce the value to '0', wherein the nutrient amounts 152 are '100% achieved'. In such an example, 'maximizing' would be selecting the combination of protocol elements 144 that results in achieving nutrient amounts 152 by minimizing the difference. As a non-limiting example, computing device 104 may assign variables relating to a set of parameters, which may correspond to autoimmune prevention components, calculate an output of mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, generating the immune protocol 144 may include generating an immune score. An "immune score," as used in this disclosure, is a numerical value, metric, parameter, and the like, described by a function, vector, matrix, or any other mathematical arrangement, which enumerates a user's current nourishment as it relates to immunological dysfunction alleviation, wherein the immune score reflects the level of user participation in the immune protocol 144. Immune score 164 may include the lifelong risk of developing immunological dysfunction. Such a score may increase with participation in immune protocol 156 and/or decrease by falling short of nutrient amounts 152, depending on criteria selected for a score increase and/or decrease. Immune score 164 may include using a machine-learning process, algorithm, and/or model to derive a numerical scale along which to provide a numerical value according to a user's immune profile 112 and participation in immune protocol 156 generated from immune profile 112. For instance, such a machine-learning model may be trained with training data, wherein training data contains data entries of nutrient amounts 152 correlated to preventing immunological dysfunction. Such a machine-learning model with said training data may be used by computing device 104 to relate nutritional input 132 to achieving some level of nutrient amount 152, and how the nutrient amount 152 relates to alleviation and prevention of dysfunction, removing allergens, reducing immune complex formation, and the like Continuing in reference to FIG. 1, in non-limiting illustrating examples, falling short of very long-chain fatty acids and vitamin D nutrient amounts 152, may have a particular effect on immune score 164 for an individual who has been classified to "IL-15 driven immunological disorder" immune category 120. Where, chronically falling short of the nutrient amount 152 results in a (−5 score) each month but falling within the nutrient amount 152 range for those two nutrients affords (+2 score for each) every month; the target amount for the preceding month may dictate the score change for each subsequent month. In such a case, a machine-learning model may derive an algorithm which dictates the amount to increase/decrease immune score 164 for that particular immune category 120 according to the nutrient amounts 152. Such a machine-learning model may be trained to identify the relationship between nutrient amounts 152 and effect on immunological dysfunction to derive an equation that relates scoring criteria. Alternatively or additionally, computing device 104 may "learn" how to provide a score and change said score based on retrieving the effect of nutrient amounts 152 (e.g. immune machine-learning model 136 outputs). Immune score 164 may then be output using the model and nutritional input 132, as inputs. Nutritional input 132 may be used to determine immune protocol 164, as well as, be used to calculate immune score 164.

Continuing in reference to FIG. 1, generating immune protocol 156 may include receiving a user preference regarding the plurality of protocol elements 144, and modifying the immune protocol 156 as a function of the user preference. A "user preference," as used in this disclosure, is a user input that designates a preference related to at least a protocol element 144. User preference 152 may include designations of protocol elements 144 to avoid and/or include such as particular food groups, condiments, spices, dietary restrictions (e.g. no animal products), cuisine type (e.g. Mediterranean foods), time of day for eating (e.g. fasting before 10 am). In this way, computing device 104 may accept an input of user preference 152 filter, sort, classify, or otherwise modify the data structure of protocol elements 144 (and associated data) and arrange the protocol elements 144 into immune protocol 156 in a custom, per-user manner. Computing device 104 may modify the plurality of protocol elements 144 as a function of the user preference 144, for instance by providing recipes with steps omitted, new steps added, or entirely new recipes altogether utilizing the same or different protocol elements 144. Computing device 104 may modify the plurality of protocol elements 144 as a function of the user preference 144 by generating a new file, based on the preference, and storing and/or retrieving the file from a database, as described in further detail below.

Figure 2:
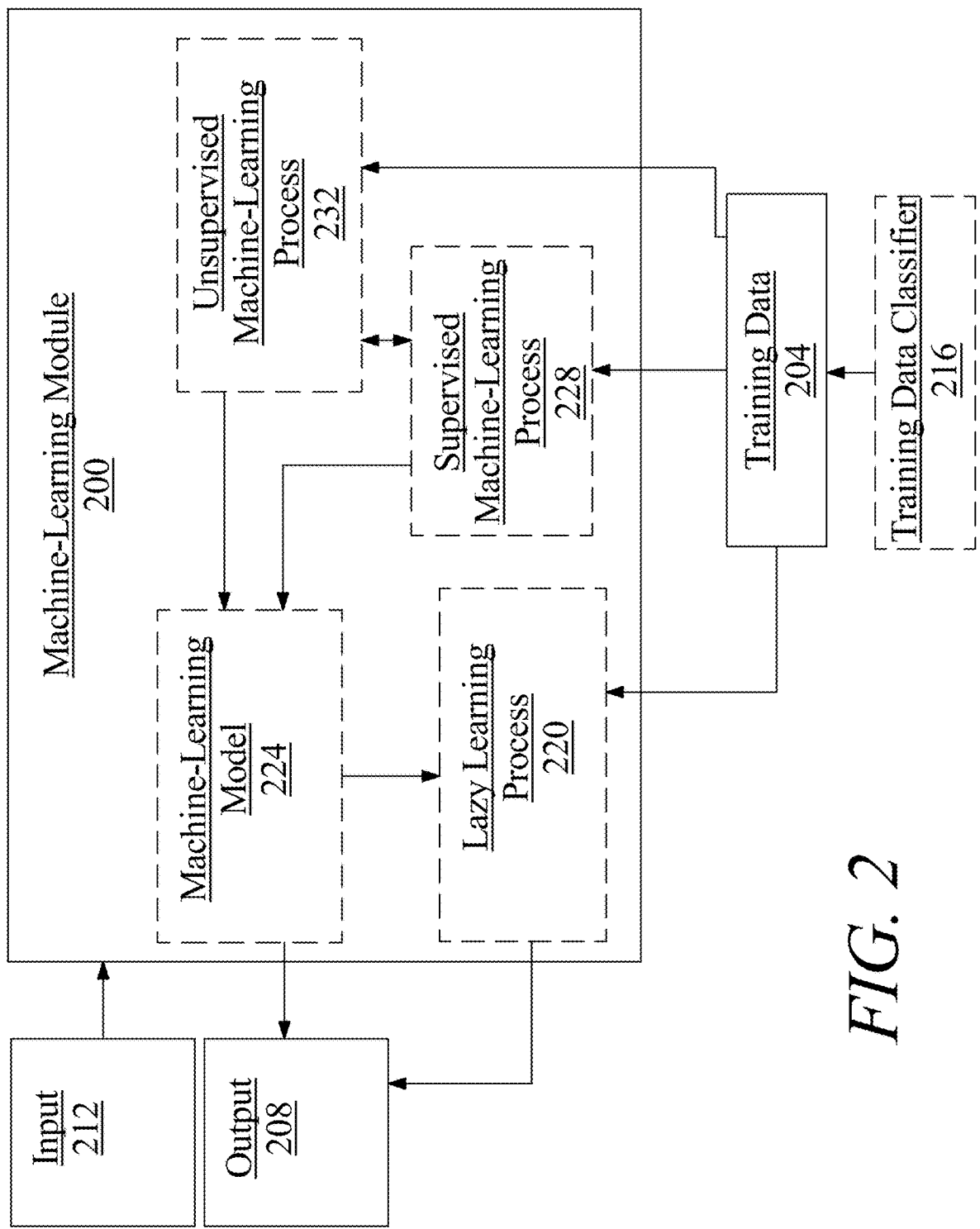
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of immune biomarkers 108 (such as patterns in cytokine levels, gene expression, and the like, as it relates to immune profile 112) and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying immune biomarker 108 elements to immune profile 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to immune profile 112, immune parameters, and/or immune score 164, and the like, as described above, to "learn" the upper and lower limits to the numerical scale, the increments to providing scoring, and the criteria for increasing and decreasing elements encompassed in the immune profile 112 and/or immune score 164, and the like A machine-learning model may be used to "learn" which elements of immune biomarkers 108 have what effect on immune profile 112, and which elements of immune profile 112 are affected by particular protocol elements 144 and the magnitude of effect, and the like The magnitude of the effect may be enumerated and provided as part of system 100, where protocol elements 144 are communicated to user for their immunological properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include an immune profile 112 (potentially classified into immune categories 120), as described above as inputs, nutrient element 120 outputs, and a ranking function representing a desired form of relationship to be detected between inputs and outputs; ranking function may, for instance, seek to maximize the probability that a given input (such as nutrient amounts 152) and/or combination of inputs is associated with a given output (immune protocol 156 that incorporate protocol elements 144 to achieve nutrient amounts 152 that are 'best' for immune category 120) to minimize the probability that a given input is not associated with a given output, for instance finding the most suitable times to consume meals, and what the meals should be, and the like Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
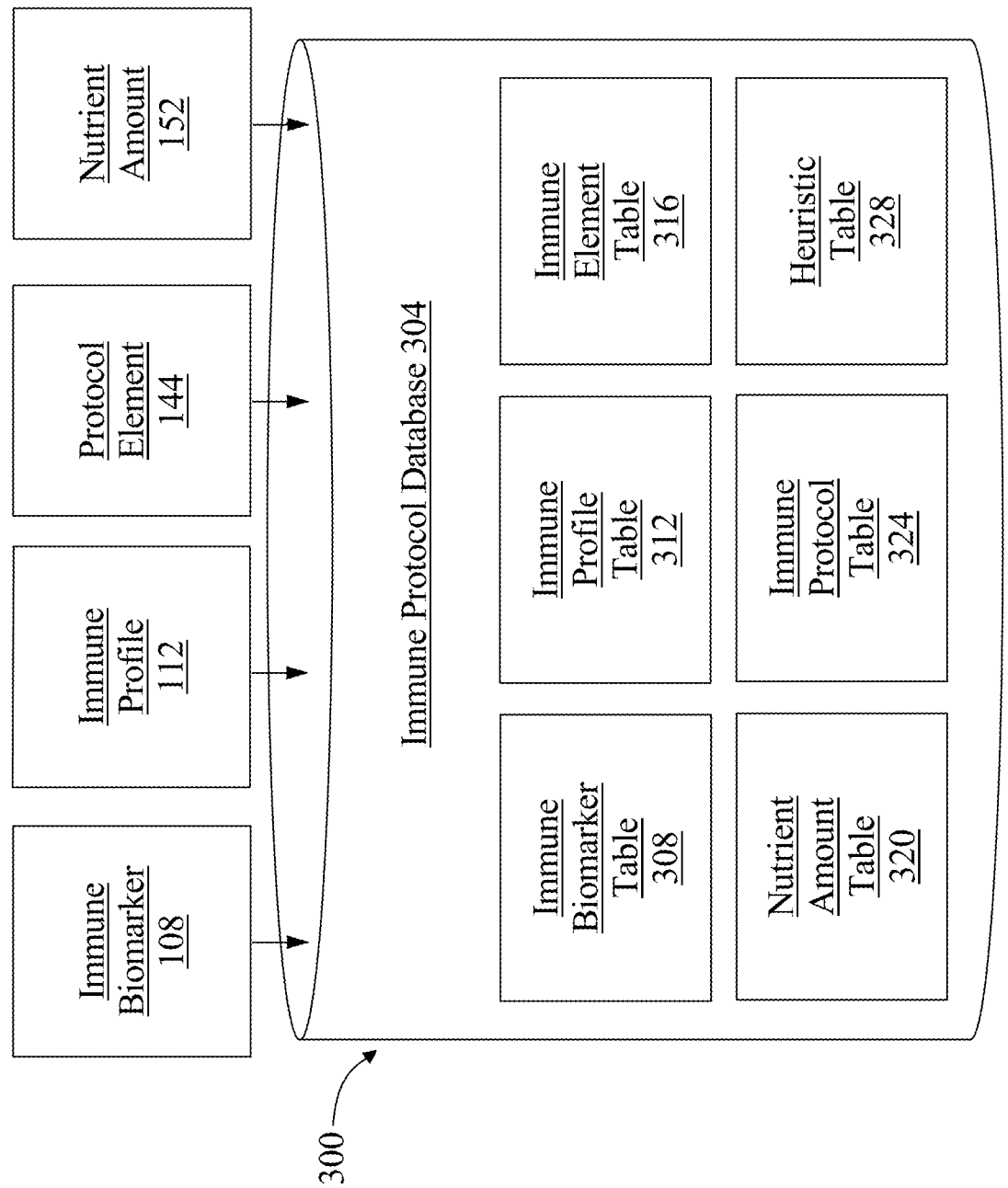
FIG. 3 is a block diagram of an immune protocol database.

Referring now to FIG. 3, a non-limiting exemplary embodiment 300 of an immune protocol database 304 is illustrated. Immune biomarker 108 for a plurality of subjects, for instance for generating a training data classifier 216, may be stored and/or retrieved in immune protocol database 304. Immune biomarker 108 data from a plurality of subjects for generating training data 204 may also be stored and/or retrieved from immune protocol database 304. Computing device 104 may receive, store, and/or retrieve training data 204, wearable device data, physiological sensor data, biological extraction data, and the like, from immune protocol database 304. Computing device 104 may store and/or retrieve immune profile machine-learning model 116, among other determinations, I/O data, models, and the like, in immune protocol database 304.

Continuing in reference to FIG. 3, immune protocol database 304 may be implemented, without limitation, as a relational database, a key-value retrieval database such as a NOSQL database, or any other format or structure for use as a database that a person skilled in the art would recognize as suitable upon review of the entirety of this disclosure. Immune protocol database 304 may alternatively or additionally be implemented using a distributed data storage protocol and/or data structure, such as a distributed hash table and the like. Immune protocol database 304 may include a plurality of data entries and/or records, as described above. Data entries in immune protocol database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, immune protocol database 304 may include, without limitation, immune biomarker table 308, immune profile table 312, protocol element table 316, nutrient amount table 320, immune protocol table 324, and/or heuristic table 328. Determinations by a machine-learning process, machine-learning model, ranking function, and/or classifier, may also be stored and/or retrieved from the immune protocol database 304. As a non-limiting example, immune protocol database 304 may organize data according to one or more instruction tables. One or more immune protocol database 304 tables may be linked to one another by, for instance in a non-limiting example, common column values. For instance, a common column between two tables of immune protocol database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of immune protocol database 304 may include, as a non-limiting example, immune biomarker table 308, which may include categorized identifying data, as described above, including genetic data, epigenetic data, microbiome data, physiological data, biological extraction data, and the like. Immune biomarker table 308 may include immune biomarker 108 categories according to gene expression patterns, SNPs, mutations, cytokine concentration, allergen data, data concerning metabolism of protocol elements 144, pharmacokinetics, nutrient absorption, and the like, categories, and may include linked tables to mathematical expressions that describe the impact of each immune biomarker 108 datum on immune profile 112, for instance threshold values for gene expression, and the like, as it relates to immunological function, immune category 120, and the like One or more tables may include immune profile table 312, which may include data regarding immune biomarker 108, thresholds, scores, metrics, values, categorizations, and the like, that system 100 may use to calculate, derive, filter, retrieve and/or store current immunological function levels, immunological dysfunctions, immune categories 120, and the like. One or more tables may include protocol element table 316, which may include data on protocol elements 144 for instance classified to immune category 120, classified to data from alike subjects with similar immune biomarker 108, immune profile 112, and the like, that system 100 may use to calculate, derive, filter, retrieve and/or store protocol elements 144. One or more tables may include nutrient amount table 320, which may include functions, model, equations, algorithms, thresholds, and the like, used to calculate or derive nutrient amounts 152 relating to immune profile 112 and/or immune category 120, may include nutrient amounts 152 organized by nutrient, nutrient classification, age, sex, symptom severity, and the like One of more tables may include immune protocol table 324, which may include protocol element 144 identifiers, elimination plan 128, reintroduction phase 140, frequency and magnitudes associated with protocol elements 144, regarding times to eat, identifiers of meals, recipes, ingredients, diet types, and the like. One or more tables may include, without limitation, a heuristic table 328, which may organize rankings, scores, models, outcomes, functions, numerical values, scales, arrays, matrices, and the like, that represent determinations, probabilities, metrics, parameters, values, and the like, include one or more inputs describing potential mathematical relationships, as described herein.

Referring now to FIGS. 4A and 4B, a non-limiting exemplary embodiment 400 of an immune profile 112 is illustrated. Immune profile 112 may include a variety of immune biomarker 108 categories, for instance 22 distinct categories, as shown in FIGS. 4A and 4B. each immune biomarker 108 may be assigned immune parameter, value, such as an arbitrary value, where some immune biomarkers 108, such as those shaded in light grey, may relate to absolute scales from [0, x], where x is a maximal value and the range of values for the immune biomarker 108 cannot be below a 'zero amount'. Some immune biomarkers 108, such as those shaded in dark grey, may relate to gene expression levels, wherein, the immune biomarker 108 is enumerated as a 'box plot' that illustrates the range of expression in a population of users organized according to, for instance tissue type. In such an example, the dashed line may relate to a 'normal threshold' above which is elevated gene expression, below which is decreased expression level. Each immune biomarker 108 may have associated with it a numerical score, or some other identifying mathematical value that computing device 104 may assign. Persons skilled in the art, upon benefit of this disclosure in full, may appreciate that for each user, any number of immune biomarkers 108 may be enumerated and assigned a value according to immune profile machine-learning model 116. Immune profile 112 may be graphed, or otherwise displayed, according to the enumeration by immune profile machine-learning model 116. For instance, each bar of the bar graph, or combinations of bar graph categories, may instruct a classification of a user's immune profile 112 to immune category 120.

Still referring now to FIGS. 4A and 4B, in non-limiting exemplary illustrations immune profile 112 may be classified to immune category 120. Some and/or all of the immune biomarkers 108 summarized in immune profile 112 may be used to classify an individual to a particular immune category 120. For instance, as shown in FIG. 4B, ten of the 22 immune biomarker 108 categories may be used to classify immune profile 112 to one or more immune categories 120. Alternatively or additionally, immune profile machine-learning model 116 may be trained to assign immune biomarker 108 to immune category 120, wherein computing device 104 may know the identity of immune category 120 according to which immune category 120 has the most identifying data points.

Figure 5:
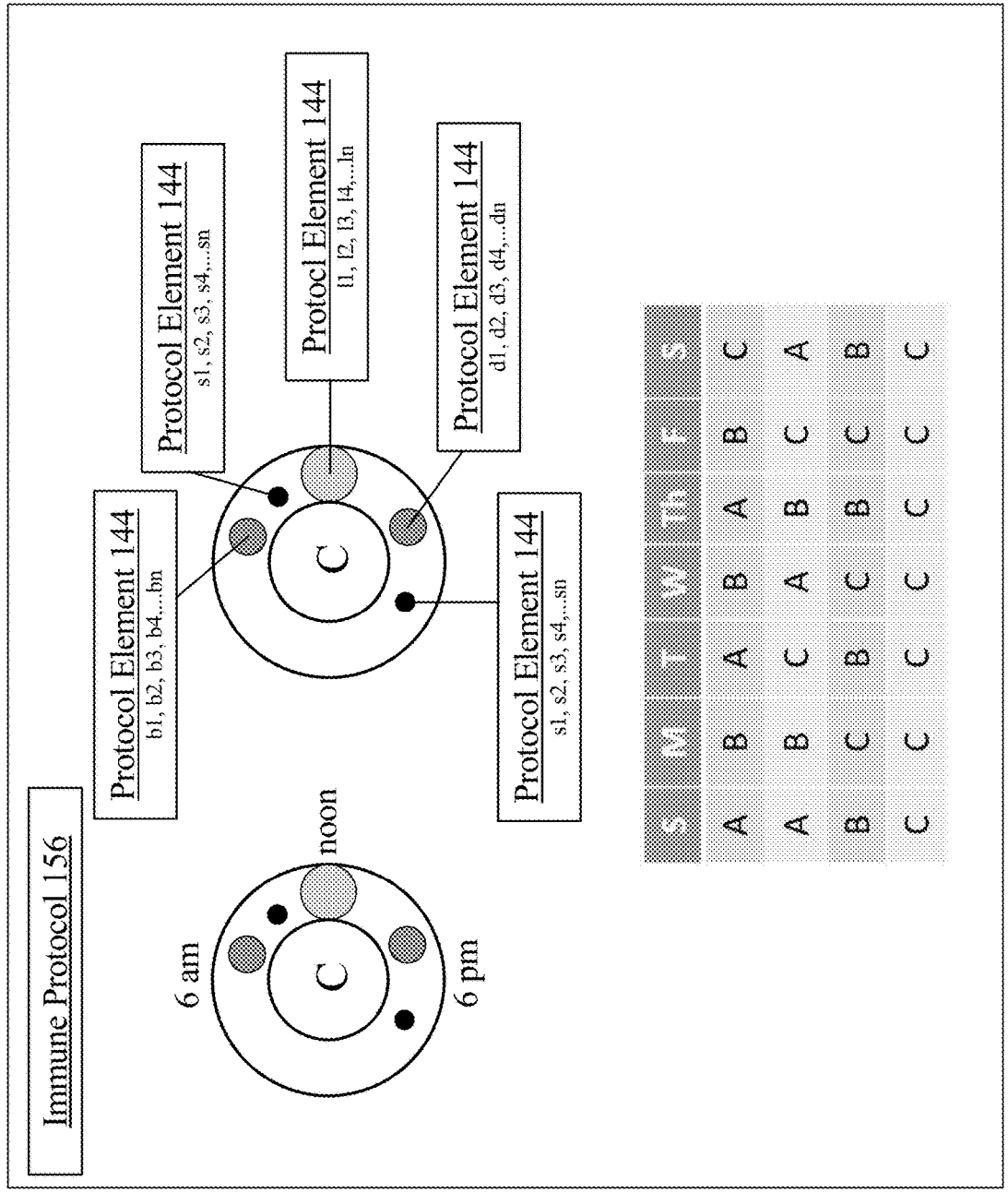
FIG. 5 is a diagrammatic representation of an immune protocol.

Referring now to FIG. 5, a non-limiting exemplary embodiment 500 of immune protocol 156 is illustrated. Immune protocol 156 may include a schedule for arranging protocol elements 144, according to for instance a 24-hour timetable, as designated on the left, where consumption is planned along a user's typical day-night cycle, beginning at ~6 am until just after 6 pm. Protocol element 144 may include breakfast (denoted as mid-sized dark grey circle), which may correspond to a file of breakfast-related plurality of protocol elements 144 (denoted b1, b2, b3, b4 . . . bn, to the nth breakfast item). Protocol element 144 may include snacks eaten throughout the day to, for instance achieve nutrient amounts 152 missing from meals (denoted as small black circles), which may correspond to a file of snacking-related plurality of protocol elements 144 (denoted s1, s2, s3, s4 . . . sn, to the nth snacking item). Protocol element 144 may include dinner (denoted as large-sized light grey circle), which may correspond to a file of dinner-related plurality of protocol elements 144 (denoted d1, d2, d3, d4 . . . dn, to the nth dinner item). Immune protocol 156 may include a variety of diets, as denoted in the monthly schedule at the bottom, Sunday through Saturday. Immune protocol 156 'C' is shown, which may be an idealistic goal for user to achieve by the end of the month, where nourishment plan 'A' and 'B' are intermediate plans intended to wean user to the 'ideal' plan. Protocol elements 144 classified by 'meal type' may be further modified by 'A' and 'B' according to user preferences 148 collected by computing device 104 throughout the process. Circle sizes, denoting Protocol element 144 classes may relate to portion sizes, which are graphed along the circle corresponding to the times they are expected to be consumed. User may indicate which protocol element 144 from each category was consumed, and when it was consumed, to arrive at immune score 164.

Figure 6:
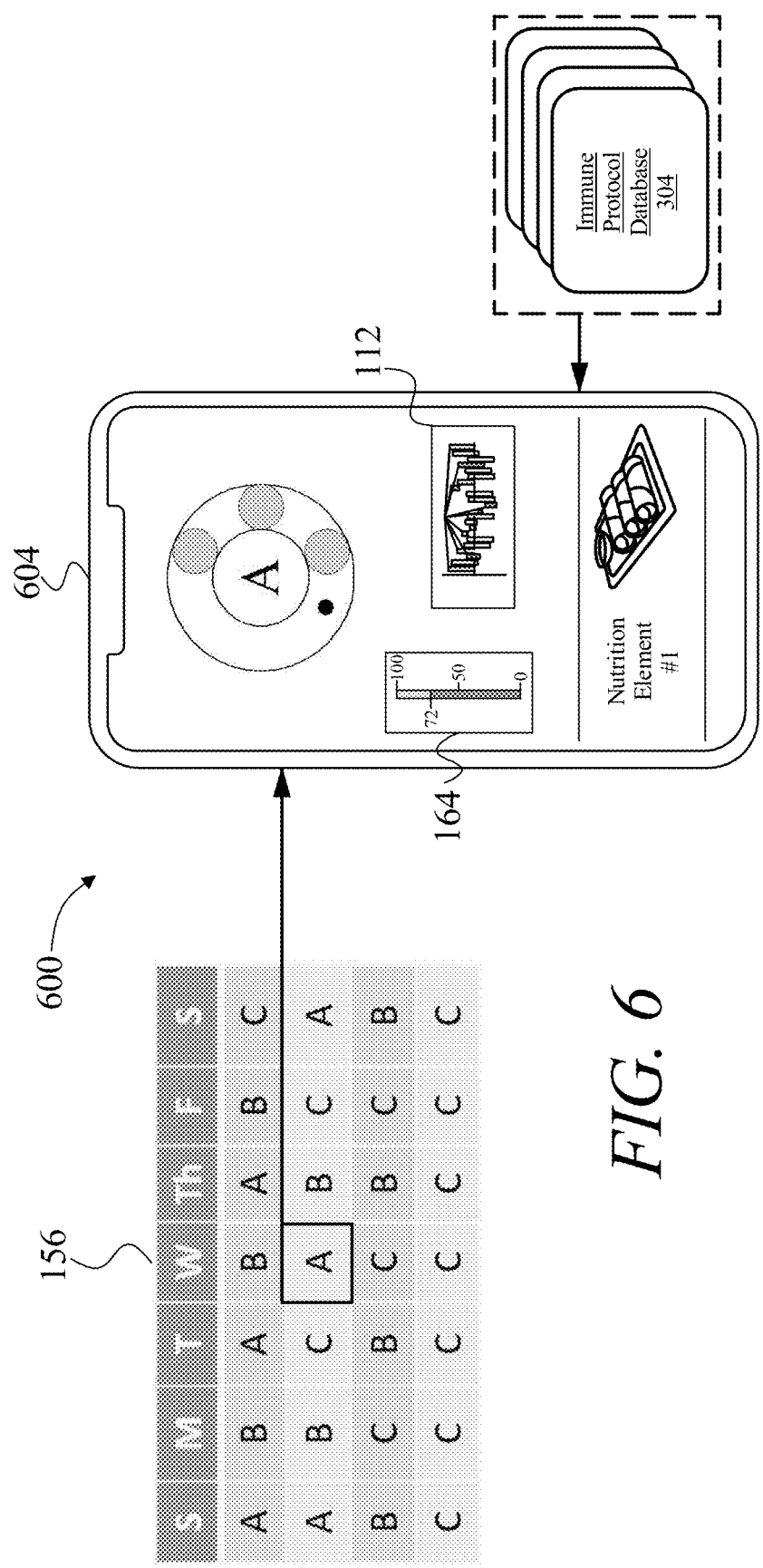
FIG. 6 is a diagrammatic representation of a user device.

Referring now to FIG. 6, a non-limiting exemplary embodiment 600 of a user device 604 is illustrated. User device 604 may include computing device 104, a "smartphone," cellular mobile phone, desktop computer, laptop, tablet computer, internet-of-things (IOT) device, wearable device, among other devices. User device 604 may include any device that is capable for communicating with computing device 104, immune protocol database 304, or able to receive, transmit, and/or display, via a graphical user interface, immune profile 112, Protocol element 144, immune protocol 156, immune score 164, among other outputs from system 100. User device 604 may provide an immune profile 112, for instance as a collection of parameters determined from immune biomarker 108 data. User device 604 may provide immune category 120 that was determined as a function of immune parameters enumerated in immune profile 112. User device 604 may provide data concerning nutrient amounts 152, including the levels of specific nutrients, nutrient ranges, nutrients to avoid, and the like User device 604 may link timing of foods to preemptive ordering interface for ordering a protocol element 144, for instance and without limitation, through a designated mobile application, mapping tool or application, and the like, and a radial search method about a user's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. User device 604 may display protocol elements 144 as a function of location. User device 604 may link immune protocol 156 to a scheduling application, such as a 'calendar' feature on user device 604, which may set audio-visual notifications, timers, alarms, and the like.

Continuing in reference to FIG. 6, user device 604 may include computing device 104, a "smartphone," cellular mobile phone, desktop computer, laptop, tablet computer, internet-of-things (IOT) device, wearable device, among other devices. User device may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Figure 7:
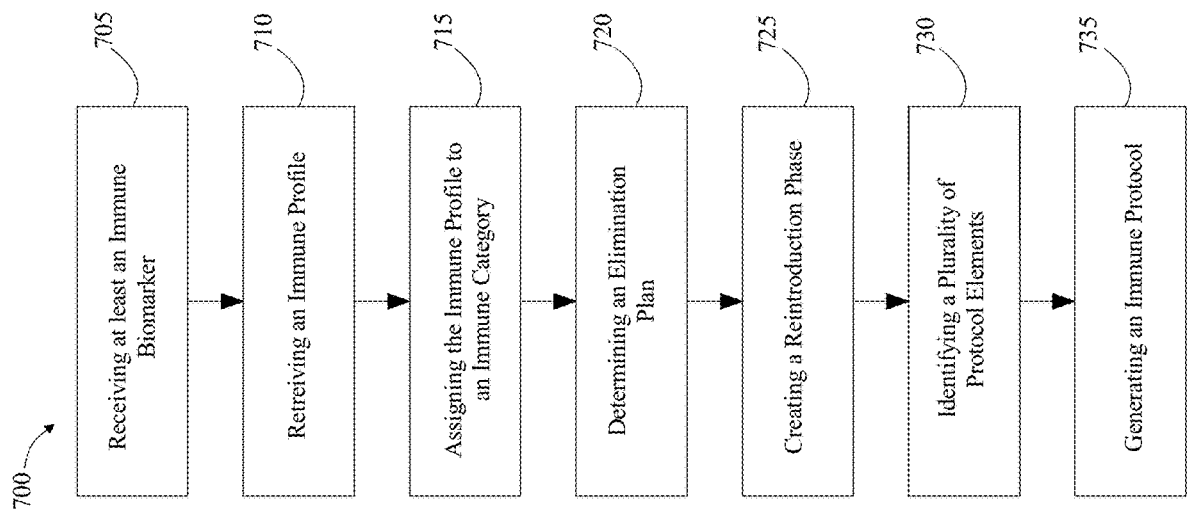
FIG. 7 is a block diagram of a workflow of a method for generating an immune protocol for identifying and reversing autoimmune disease.

Referring now to FIG. 7, an exemplary embodiment 700 of a method for generating an immune protocol for identifying and reversing autoimmune disease is illustrated. At step 705, the method includes receiving, by a computing device 104, at least an immune biomarker 108; this may be implemented, without limitation, as described above in FIGS. 1-6.

Still referring to FIG. 7, at step 710, method includes retrieving, by the computing device 104, an immune profile 112 related to the user. Retrieving the immune profile 112 related to the user may include training an immune profile machine-learning model 116 with the immune profile training data that includes a plurality of data entries wherein each entry correlates immune biomarkers 108 to a plurality of immune parameters, and generating the immune profile 112 as a function of the immune profile machine-learning model 116 and the at least an immune biomarker 108; this may be implemented, without limitation, as described above in FIGS. 1-6.

Continuing in reference to FIG. 7, at step 715, method includes assigning, by the computing device 104, the immune profile 112 to an immune category 120, wherein the immune category 120 is a determination about a current immunological state of the user according to the at least an immune biomarker 108. Assigning the immune profile 112 to an immune category 120 may include classifying the immune profile 112 to an immune category 120 using an immune classification machine-learning process 124 and assigning the immune category 120 as a function of the classifying; this may be implemented, without limitation, as described above in FIGS. 1-6.

Continuing in reference to FIG. 1, at step 720, method includes determining, by the computing device 104, using the immune category 120 and the immune profile 112, an elimination plan 128, wherein determining the elimination plan 128 includes identifying an effect on the immune profile 120 for each nutrition element of a plurality of nutrition elements, wherein the plurality of nutrition elements have been consumed by the user, determining, of the identified effect, at least a nutrition element that may contribute to the immune category; this may be implemented, without limitation, as described above in FIGS. 1-6. Identifying an effect on the immune profile 112 for each nutrition element of a plurality of nutrition elements may include receiving nutritional input 132 from the user. Determining at least a nutrition element that may contribute to the immune category 120 may include receiving immune training data, training an immune machine-learning model 136 with immune training data that includes a plurality of data entries wherein each entry correlates a plurality of nutrition amounts to immune biomarkers 108 and determining at least a nutrition element that may contribute to the immune category 120 as a function of the immune machine-learning model 136 and the nutritional input 132 from the user; this may be implemented, without limitation, as described above in FIGS. 1-6.

Continuing in reference to FIG. 7, at step 725, method includes creating, by the computing device 104, using the elimination plan 128, a reintroduction phase 140, wherein creating the reintroduction phase 140 includes identifying a frequency associated with the at least a nutrition element determined in the elimination plan 128 and identifying a magnitude associated with the at least a nutrition element determined in the elimination plan 128. Identifying the frequency associated with the at least a nutrition element determined in the elimination plan 128 may include calculating a consumption time of the at least a nutrition elements as a function of the identified effect in the elimination plan 128. Identifying the magnitude associated with the at least a nutrition element may include calculating a serving size of the at least a nutrition element as a function of the identified effect in the elimination plan 128; this may be implemented, without limitation, as described above in FIGS. 1-6.

Continuing in reference to FIG. 7, at step 730, method includes identifying, by the computing device 104, a plurality of protocol elements 144, wherein each protocol element 144 contains at least a nutrient amount intended to prevent autoimmune disease. Identifying a plurality of protocol elements 144 may include training a nutrition machine-learning process 148 with training data, wherein training data includes a plurality of data entries that correlates a plurality of nutrient effects to a plurality of nutrient amounts 152 for each immune category 120, calculate the at least a nutrient amount as a function of the immune category 120 of the user, and identifying the plurality of protocol elements 144 according to the nutrition machine-learning process 148 and the at least a nutrient amount 152; this may be implemented, without limitation, as described above in FIGS. 1-6.

Continuing in reference to FIG. 7, at step 735, method includes generating, by the computing device 104, an immune protocol 156 using, using the elimination plan 128, the reintroduction phase 140, and the plurality of protocol elements 144. Generating the immune protocol 156 may include generating an objective function 160 with the plurality of protocol elements 144, wherein the objection function 160 outputs at least an ordering of the plurality of protocol elements 144 according to constraints in the reintroduction phase 140. Generating the immune protocol 156 may include generating an immune score 164; this may be implemented, without limitation, as described above in FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
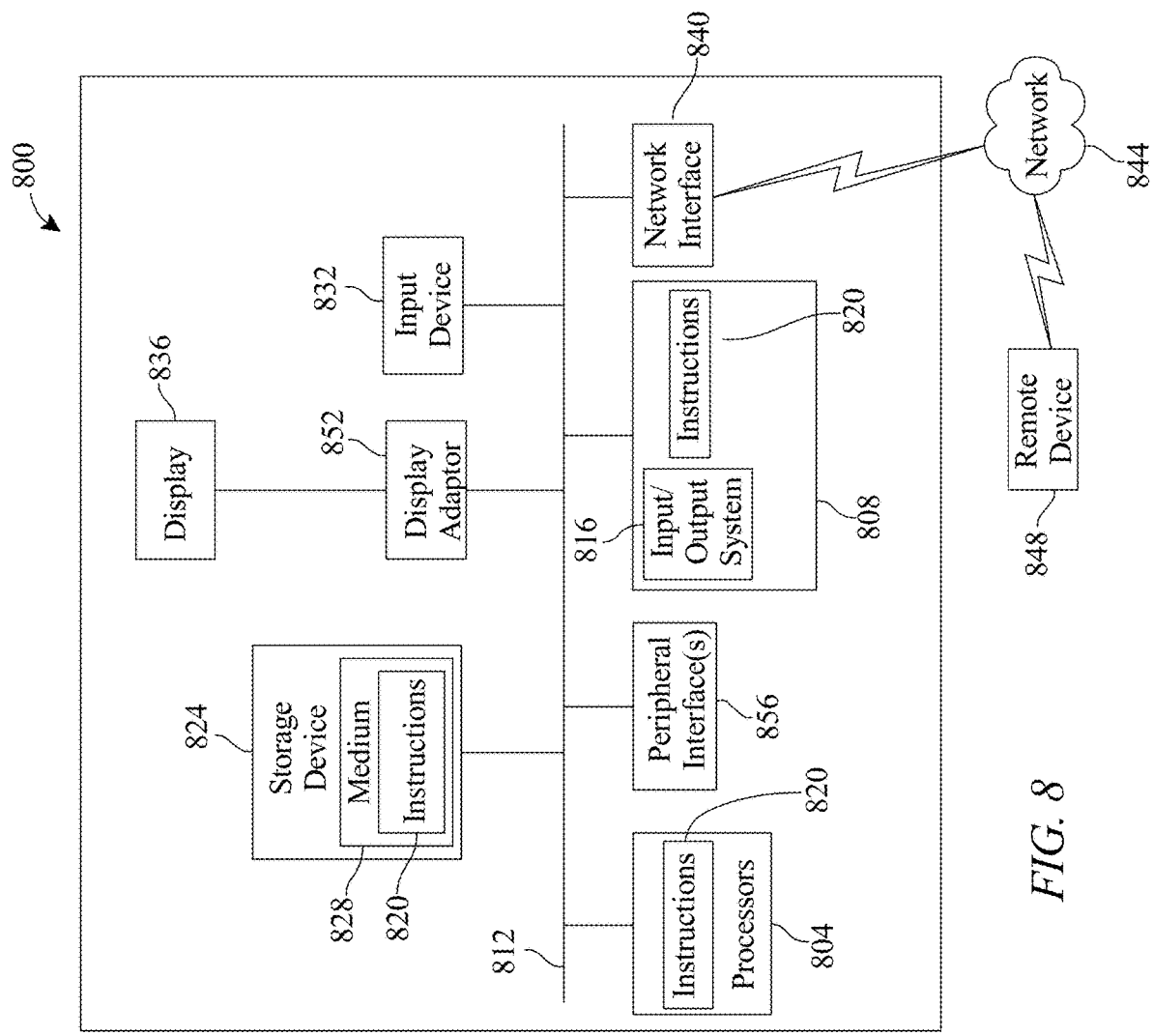
FIG. 8 is a block diagram of a computing system that can be used to implement any one or more of the methodologies disclosed herein and any one or more portions thereof.

Referring now to FIG. 8, a diagrammatic representation of one embodiment of a computing device in the exemplary form of a computer system 800 within which a set of instructions for causing a control system to perform any one or more of the aspects and/or methodologies of the present disclosure may be executed is illustrated. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Continuing in reference to FIG. 8, processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Continuing in reference to FIG. 8, memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Continuing in reference to FIG. 8, computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Continuing in reference to FIG. 8, computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

Continuing in reference to FIG. 8, a user may also input commands and/or other information to computer system 800 via storage device 824 (e.g., a removable disk drive, a flash drive, and the like) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, and the like) may be communicated to and/or from computer system 800 via network interface device 840.

Continuing in reference to FIG. 8, computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an immune protocol for identifying and reversing immune disease, the system comprising:
 a computing device, wherein the computing device is configured to:
  receive at least an immune biomarker as an input;
  retrieve an immune profile related to a user, wherein retrieving the immune profile related to the user further comprises:
   training an immune profile machine-learning model with training data including a plurality of data entries wherein each entry correlates immune biomarkers to a plurality of immune parameters; and
   outputting the immune profile as a function of the immune profile machine-learning model and the at least an immune biomarker;
  assign the immune profile to an immune category;
  determine, using the immune category and the immune profile, an elimination plan, wherein determining the elimination plan includes:
   identifying an effect on the immune profile for each nutrition element of a plurality of nutrition elements, wherein the plurality of nutrition elements have been consumed by the user;
   determining, as a function of the identified effect, at least a nutrition element that contributes to the immune category;
  create, using the elimination plan, a reintroduction phase, wherein creating the reintroduction phase includes:
   identifying a frequency associated with the at least a nutrition element determined in the elimination plan; and
   identifying a magnitude associated with the at least a nutrition element determined in the elimination plan, wherein identifying the magnitude associated with the at least a nutrition element comprises calculating a serving size of the at least a nutrition element as a function of the identified effect in the elimination plan;
  output a plurality of protocol elements, wherein each protocol element contains at least a nutrient amount intended to immunological dysfunction; and
  generate an immune protocol as a function of the elimination plan, the reintroduction phase, and the plurality of protocol elements.

2. The system of claim 1, wherein assigning the immune profile to the immune category further comprises:
 classifying the immune profile to the immune category using an immune classification machine-learning process; and
 assigning the immune category as a function of the classifying.

3. The system of claim 1, wherein identifying the effect on the immune profile further comprises receiving a nutritional input from the user.

4. The system of claim 3, wherein determining the at least a nutrition element that contributes to the immune category further comprises:
 receiving immune training data;
 training an immune machine-learning model with the immune training data including a plurality of data entries wherein each entry correlates a plurality of nutrition amounts to immune biomarkers; and
 determining the at least a nutrition element that contributes to the immune category as a function of the immune machine-learning model and the nutritional input from the user.

5. The system of claim 1, wherein identifying the frequency associated with the at least a nutrition element determined in the elimination plan further comprises calculating a consumption time of the at least a nutrition element as a function of the identified effect in the elimination plan.

6. The system of claim 1, wherein identifying the plurality of protocol elements further comprises:
 training a nutrition machine-learning process with training data, wherein training data includes a plurality of data entries that correlates a plurality of nutrient effects to the plurality of nutrient amounts for each immune category;
 calculate the at least a nutrient amount as a function of the immune category of the user; and
 identifying the plurality of protocol elements according to the nutrition machine-learning process and the at least a nutrient amount.

7. The system of claim 1, wherein generating the immune protocol further comprises generating an objective function with the plurality of protocol elements, wherein the objection function outputs at least an ordering of the plurality of protocol elements according to constraints in the reintroduction phase.

8. The system of claim 1, wherein generating the immune protocol further comprises generating an immune score.

9. A method for generating an immune protocol for identifying and reversing immune disease, the method comprising:
 receiving, by a computing device, at least an immune biomarker as an input;
 retrieving, by the computing device, an immune profile related to a user, wherein retrieving the immune profile related to the user further comprises:
  training an immune profile machine-learning model with training data including a plurality of data entries wherein each entry correlates immune biomarkers to a plurality of immune parameters; and
  outputting the immune profile as a function of the immune profile machine-learning model and the at least an immune biomarker;
 assigning, by the computing device, the immune profile to an immune category;
 determining, by the computing device, using the immune category and the immune profile, an elimination plan, wherein determining the elimination plan includes:

identifying an effect on the immune profile for each nutrition element of a plurality of nutrition elements, wherein the plurality of nutrition elements have been consumed by the user;

determining, as a function of the identified effect, at least a nutrition element that contributes to the immune category;

creating, by the computing device, using the elimination plan, a reintroduction phase, wherein creating the reintroduction phase includes:

identifying a frequency associated with the at least a nutrition element determined in the elimination plan; and identifying a magnitude associated with the at least a nutrition element determined in the elimination plan, wherein identifying the magnitude associated with the at least a nutrition element further comprises calculating a serving size of the at least a nutrition element as a function of the identified effect in the elimination plan;

outputting, by the computing device, a plurality of protocol elements, wherein each protocol element contains at least a nutrient amount intended to immunological dysfunction; and generating, by the computing device, an immune protocol as a function of the elimination plan, the reintroduction phase, and the plurality of protocol elements.

10. The method of claim 9, wherein assigning the immune profile to the immune category further comprises:

classifying the immune profile to the immune category using an immune classification machine-learning process; and assigning the immune category as a function of the classifying.

11. The method of claim 9, wherein identifying the effect on the immune profile further comprises receiving a nutritional input from the user.

12. The method of claim 11, wherein determining the at least a nutrition element that contributes to the immune category further comprises:

receiving immune training data;

training an immune machine-learning model with the immune training data including a plurality of data entries wherein each entry correlates a plurality of nutrition amounts to immune biomarkers; and determining the at least a nutrition element that contributes to the immune category as a function of the immune machine-learning model and the nutritional input from the user.

13. The method of claim 9, wherein identifying the frequency associated with the at least a nutrition element determined in the elimination plan further comprises calculating a consumption time of the at least a nutrition element as a function of the identified effect in the elimination plan.

14. The method of claim 9, wherein identifying the plurality of protocol elements further comprises:

training a nutrition machine-learning process with training data, wherein training data includes a plurality of data entries that correlates a plurality of nutrient effects to the plurality of nutrient amounts for each immune category;

calculate the at least a nutrient amount as a function of the immune category of the user; and identifying the plurality of protocol elements according to the nutrition machine-learning process and the at least a nutrient amount.

15. The method of claim 9, wherein generating the immune protocol further comprises generating an objective function with the plurality of protocol elements, wherein the objection function outputs at least an ordering of the plurality of protocol elements according to constraints in the reintroduction phase.

16. The method of claim 9, wherein generating the immune protocol further comprises generating an immune score.

* * * * *